United States Patent
Giordani et al.

(10) Patent No.: US 8,633,208 B2
(45) Date of Patent: Jan. 21, 2014

(54) 6-1H-IMIDAZO-QUINAZOLINE AND QUINOLINES DERIVATIVES, NEW MAO INHIBITORS AND IMIDAZOLINE RECEPTOR LIGANDS

(75) Inventors: Antonio Giordani, Pavia (IT); Marco Lanza, Lecco (IT); Gianfranco Caselli, Milan (IT); Stefano Mandelli, Casatenovo (IT); Simona Zanzola, Milan (IT); Francesco Makovec, Lesmo (IT); Lucio Claudio Rovati, Monza (IT)

(73) Assignee: Rottapharm S.p.A, Milan (IT)

( * ) Notice: Subject to any disclaimer, the term of this patent is extended or adjusted under 35 U.S.C. 154(b) by 343 days.

(21) Appl. No.: 12/999,862

(22) PCT Filed: Jun. 20, 2008

(86) PCT No.: PCT/EP2008/057908
§ 371 (c)(1), (2), (4) Date: Dec. 17, 2010

(87) PCT Pub. No.: WO2009/152868
PCT Pub. Date: Dec. 23, 2009

(65) Prior Publication Data
US 2011/0118289 A1 May 19, 2011

(51) Int. Cl.
*A01N 43/54* (2006.01)
*A01N 43/42* (2006.01)
*A61K 31/517* (2006.01)
*A61K 31/44* (2006.01)
*C07D 239/72* (2006.01)
*C07D 401/00* (2006.01)
*C07D 403/00* (2006.01)
*C07D 413/00* (2006.01)
*C07D 417/00* (2006.01)
*C07D 419/00* (2006.01)
*C07D 233/00* (2006.01)

(52) U.S. Cl.
USPC ........ 514/266.2; 514/283; 544/283; 544/284; 548/335.1

(58) Field of Classification Search
USPC ............... 514/266.2, 396; 544/283, 284; 548/335.1
See application file for complete search history.

(56) References Cited

U.S. PATENT DOCUMENTS 7,994,181 B2 * 8/2011 Giordani et al. ........... 514/266.2

FOREIGN PATENT DOCUMENTS

| EP | 1 571 142 A1 | 9/2005 |
| WO | 94/22852 A1 | 10/1994 |
| WO | 01/70703 A2 | 9/2001 |
| WO | 2008/014822 A1 | 2/2008 |

OTHER PUBLICATIONS

Muller et al. "The cyclooxygenase-2 inhibitor celecoxib has therapeutic effects in major depression: results of a double-blind, radomized, placebo controlled, add-on pilot study to reboxetine" Mol Psychiatry, Jul. 2006, vol. 11, No. 7, pp. 680-684.*
Mariana P. Ziedan, et al., Evidence for imidazoline receptors involvement in the agmatine antidepressant-like effect in the forced swimming test (2007), pp. 125-131, European Journal of Pharmacology 565, SC Brazil.
Guillaume Vaiva, et al., Treatment of comorbid opiate addiction and attention-deficit hyperactivity disorder (residual type) with moclobemide A case report, Progress in Neuro-Psychopharmacology & Biological Psychiatry 26, (2002) 609-611, Lille, France.
Stephen A. Hitchcock, et al., Selectivity in Palladium(0)-Catalyzed Cross-Coupling Reactions: Application to a Tandem Stille Reaction, Tetrahedron Letters, 1995, pp. 9085-9088, vol. 36, No. 50, Indianapolis, IN.
TP George, et al., Monoamine Oxidase Inhibition for Tobacco Pharmacotherapy, Clinical Pharmacology & Therapeutics, Apr. 2008, pp. 619-621, vol. 83, No. 4, Toronto, Ontario, Canada.
Jingping Liu, et al., A Modified Procedure for the Synthesis of 1-Arylimidazoles, Synthesis 2003, pp. 2661-2666, No. 17, New York.
Lucien Steru, et al., The tail suspension test: A new method for screening antidepressants in mice, Psychopharmacology (1985) 85: 367-370, Paris Cedex 13, France.

(Continued)

*Primary Examiner* — Kendra D Carter
(74) *Attorney, Agent, or Firm* — Sughrue Mion, PLLC

(57) ABSTRACT

The present invention is directed to 6-(1H-imidazo-1-yl)-2-aryl and 2-heteroaryl quinazoline and quinolines derivatives, compounds of formula (I), their pharmaceutical acceptable salts and solvates and corresponding pharmaceutical compositions, that acts as Monoamine Oxidase (MAO) inhibitors and Imidazoline Receptor ligands:

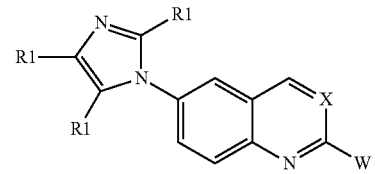

wherein: X is independently selected from —CH group or a nitrogen atom (—N), W is independently selected from an aryl group, an heteroaryl group, or a benzocondensed heteroaryl group such as 1,3-benzodioxole, benzofuran, 2,3-dihydrobenzofuran, benzothiophene, 2,3-dihydrobenzothiophene, indole, 2,3-dihydroindole, benzimidazole, benzoxazole, benzothiazole, 2H-3,4-dihydrobenzopyran, [1,4]-benzodioxine, 2,3-dihydro-[1,4]-benzodioxine (1,4-benzodioxan). $R_1$ is independently selected from hydrogen (—H), $C_1$-$C_4$ alkyl, hydroxymethyl (—$CH_2OH$), aminomethyl (—$CH_2NH_2$), alkylaminomethyl [$CH_2NH(R_2)$], or di-alkylaminomethyl [$CH_2N(R_2)_2$], trifluoromethyl (—$CF_3$).
Compounds of formula (I) elicited a pharmacological profile suitable for the clinical treatment of depression and related disorders, Parkinson disease, drug abuse, and morphine tolerance and dependence.

3 Claims, No Drawings

(56) References Cited

OTHER PUBLICATIONS

Sheila M. Mackenzie, et al., Triazines and Related Products. Part VI.1 Synthesis and Properties of 4-Amino-2(2h)-imino-s-triazino [1,2-c] [1,2,3]-benzotriazines, J. Chem. Soc. (C), 1970, pp. 2298-2308, Edinburgh 1.

Elisabeth J. Houtsmuller, et al., Transdermal selegiline and intravenous cocaine: safety and interactions, Psychopharmacology (2004), pp. 172:31-40, Baltimore, MD.

Katharine Walker, et al., Animal models for pain research, Molecular Medicine Today, Jul. 1999, pp. 319-321, (vol. 5), London, UK.

Antonio Miralles, et al., High-affinity binding of β-carbolines to imidazoline I $_{2B}$ receptors and MAO-A in rat tissues: Norharman blocks the effect of morphine withdrawal on DOPA/noradrenaline synthesis in the brain, European Journal of Pharmacology 518 (2005) 234-242, Palma de Mallorca, Spain.

C.J. Woolf, et al., Cytokines, nerve growth factor and inflammatory hyperalgesia: the contribution of tumour necrosis factor α, British Journal of Pharmacology, (1997), 121, pp. 417-424, London.

Moussa B.H., et al., Monoamine oxidase: isoforms and inhibitors in Parkinson's disease and depressive illness, British Journal of Pharmacology, (2006) 147, pp. S287-S296, 2006, London.

Udo Bonnet, Moclobemide: Therapeutic Use and Clinical Studies, CNS Drug Reviews, 2003, vol. 9, No. 1, pp. 97-140, Essen, Germany.

K. Grasing, et al., Effects of high-dose selegiline on morphine reinforcement and precipitated withdrawal in dependent rats, Behavioural Pharmacology 2005, 16:1-13, Kansas City, MO.

Marion M. Bradford, A Rapid and Sensitive Method for the Quantitation of Microgram Quantities of Protein Utilizing the Principle of Protein-Dye Binding, Analytical Biochemistry 72 (1976), pp. 248-254, Athens, Georgia.

Alan Doris, et al., Depressive Illness, Lancet 1999, 354:1369-75, Edinburgh, UK.

David J. Connolly, et al., Preparation and Resolution of a Modular Class of Axially Chiral Quinazoline-Containing Ligands and Their Application in Asymmetric Rhodium-Catalyzed Olefin Hydroboration, JOC Article, J. Org. Chem. 2004,69, pp. 6572-6589, Ruhr, Germany.

Mimi L. Quan, et al., Discovery of 1-(3'-Aminobenzisoxazol-5'-yl)-3-trifluoromethyl-*N*-[2-fluoro-4- [2'-dimethylaminomethyl) imidazol-1-yl]phenyl]-1*H*-pyrazole-5-carboxyamide Hydrochloride (Razaxaban), a Highly Potent, Selective, and Orally Bioavailable Factor Xa Inhibitor, Articles, J. Med. Chem 2005, 48, pp. 1729-1744, Princeton, New Jersey.

Christian Leschke, et al., Synthesis and Histamine $H_1$ Receptor Agonist Activity of a Series of 2-Phenylhistamines, 2-Heteroarylhistamines, [†] and Analogues[‡], J. Med. Chem. 1995, 38, 1287-1294, Paris, France.

Jonathan R.T. Davidson, M.D., Pharmacotherapy of Social Anxiety Disorder: What Does the Evidence Tell Us?, J. Clin Psychiatry 2006;67 [suppl 12]:20-26, Durham, NC.

Eckhard Baston, et al., 6-Substituted 1*H*-quinolin-2-ones and 2-methoxy-quinolines: synthesis and evaluation as inhibitors of steroid 5α reductases types 1 and 2, Eur. J. Med. Chem. 35 (2000), pp. 931-940, Saarbrücken, Germany.

Reza Sharif Naeini, et al., Remodelling of spinal nociceptive mechanisms in an animal model of monoarthritis, European Journal of Neuroscience, 2005, pp. 2005-2015, vol. 22, Montreal QC, Canada.

Neil T. Burford, et al., Specific G protein activation and μ-opioid receptor internalization caused by morphine, DAMGO and endomorphin I, European Journal of Pharmacology 342 (1998) 123-126, San Francisco, CA.

A Wasik et al, The Effect of an Endogenous Compound 1-Methyl-1,2,3,4-Tetrahydroisoquinoline on Morphine-Induced Analgesia, Dependence and Neurochemical Changes in Dopamine Metabolism in Rat Brain Structures, Department of Biochemistry, Institute of Pharmacology Polish Academy of Sciences, Apr. 23, 2007, 13 pages, Krakow, Poland.

Dr. med. Dr. rer. nat. Drs. h.c. Ernst Mutschler, et al., "Chapter 1.2.3.5: (Selektive) Noradrenalin-Wiederaufnahmehemmer (NRI=noradrenaline reuptake inhibitors)", Mutschler Arzneimittelwirkunger: Lehrbuch der Pharmakologie und Toxikologie, Jan. 1, 2001, pp. 178-179, XP007906836, ISBN: 978-3-8047-1763-3, Wissenschaftliche Verlagsgesellschaft mbH Stuttgart 2001.

International Search Report for International Application No. PCT/EP2008/057908 dated Mar. 16, 2009.

Written Opinion for International Application No. PCT/EP2008/057908 dated Mar. 16, 2009.

* cited by examiner

6-1H-IMIDAZO-QUINAZOLINE AND QUINOLINES DERIVATIVES, NEW MAO INHIBITORS AND IMIDAZOLINE RECEPTOR LIGANDS

CROSS REFERENCE TO RELATED APPLICATIONS

This application is a National Stage of International Application No. PCT/EP2008/057908 filed Jun. 20, 2008, the content of which is incorporated herein by reference in its entirety.

The present invention is directed to 6-(1H-imidazo-1-yl)-2-aryl and 2-heteroaryl quinazoline and quinolines derivatives acting as Monoamine Oxidase (MAO) inhibitors and Imidazoline Receptor ligands, to a process for their preparation, and to the use of such compounds, their pharmaceutical acceptable salts and solvates, and corresponding pharmaceutical compositions, for the pharmacological treatment of depression and related disorders, Parkinson disease, drug abuse, and morphine tolerance and dependence.

BACKGROUND

Depression is a common and harmful mood disorder that affects emotion, cognition, and behaviour; rather than a clearly defined disease, depression involves a wide spectrum of disorders ranging from the feeling of unhappiness to more severe incapacitating disorders such as Clinical depression (also called major-depressive disorder or unipolar depression), Dysthymic disorder, Bipolar disorder, Atypical depression, Psychotic depression, Postpartum depression and Seasonal affective disorder (A. Doris et al. Depressive illness, Lancet, 1999, 354, 9187, 1369). According to the World Health Organization (WHO), depression is characterized by depressed mood, loss of interest or pleasure, feelings of guiltiness or low-self-esteem, disturbances in sleep and/or appetite, poor concentration. Major depressive disorder, also known as major depression, is the most common type of depression with about 10-25% lifetime risk in the industrialized countries population. It is characterized by a combination of symptoms and disabling conditions that seriously interfere with work and family life, sleeping and eating habits, and with the general health of the patient. Dysthymic disorder, also called dysthymia, is characterized by long-term less severe symptoms that may not disable a person but can prevent a person of feeling well thus impacting the social life. Bipolar disorder, also called manic-depressive illness, is characterized with cycling mood changes from extreme highs (e.g., mania) to extreme lows (e.g., depression). Atypical Depression is a subtype of dysthymia and major depression characterized by mood reactivity and vegetative symptoms like over-eating and over-sleeping. Psychotic depression, occurs when a severe depressive illness is accompanied by some form of psychosis, hallucinations, and delusions. Postpartum depression, which affects 10-15% of women, is diagnosed if a major depressive episode occurs within one month after the childbirth, the disease has similar symptoms as clinical depression. Seasonal affective disorder, is characterized by the onset of a depressive illness during the winter months. Depressive and anxiety symptoms often overlap. Anxiety disorders comprise post-traumatic stress disorder, panic disorder, agoraphobia, social phobia, obsessive compulsive disorder. Panic disorder is classified as an anxiety disorder since anxiety is the predominant symptom, panic attacks are discrete episodes consequence of a panic disorder. The development of severe phobic symptoms matches the escalation in frequency and intensity of panic attacks, leading to a severe and disabling disorder which impacts the patient professional, social and familial life. Depression may be a primary condition or can co-exists with other serious medical illnesses such as heart disease, stroke, cancer, diabetes and Parkinson's disease. Clinical studies have shown that people who have depression in addition to another serious medical illness tend to have more severe symptoms of both depression and the medical illness, more difficulty adapting to their medical condition, and more medical costs than those without co-existing depression. Research has provided evidences that treating the depression can also help at improving the outcome of treating the co-occurring illness. Alcohol, tobacco and drug abuse may also co-occur with depression. In fact, statistical research indicated that the co-existence of mood disorders is pervasive among the people involved in alcohol, tobacco and drug abuse. Depressive disorders are extremely common, affecting about 120 million people worldwide each year. According to WHO depression is a leading cause of disability and it is the fourth most important contributor to the global burden of disease. Morbidity and mortality in depressed patients are higher than in normal subjects. According to the National Institute of Mental Health (NIMH) recent studies highlighted how persons with major depression were four times as likely to suffer of a heart attack as not depressed controls. According to NIMH direct and indirect social costs of depression amounted for the year 1990 to about 30 billion USD, being indirect costs represented by decreased worker productivity and disruption of personal, professional and family relationships. An analogue evaluation in Europe for year 2004 high-lighted a social cost of 118 billion Euro, pointing out depression as the most costly brain disorder in Europe.

According to the monoamine hypothesis, depression is caused by an imbalance of these neurotransmitters in the brain. One pharmacological strategy aimed at overcoming this imbalance consists of inhibiting the enzyme Monoamine Oxidase (MAO; EC 1.4.3.4). The monoamine neurotransmitters serotonin (5-HT), norepinephrine (NE) and dopamine are widely distributed within the brain and are involved in the regulation of mood, cognition, sleep, anxiety and social behavior. Dysfunctions in mechanisms controlling these neurotransmitters are often associated with most major psychiatric disorders and drugs targeting monoamine neurotransmitters have been and are widely investigated for the treatment of depression. MAO is a FAD dependent enzyme (flavoprotein) mainly located in outer mitochondrial membranes of neurons and glial cells as well as in other cells of the periphery (i.e.: epatocytes), where it catalyzes the oxidative deamination of neurotransmitter, xenobiotic and endogenous amines. The antidepressant approach for MAO inhibitors is based on the fact that by inhibiting the enzyme activity, deactivation of these endogenous neurotransmitters is prevented thus increasing both their synaptic concentration and duration of action. There are two isoforms of MAO: MAO-A which preferentially deaminates serotonin, norepinephrine and epinephrine, but also amines present in foods like tyramine, and MAO-B which preferentially deaminates dopamines, phenylethylamines and benzylamines (B. H. Moussa, British J. Pharmacolgy, 2006, 147, S287-296). The first generation of MAO inhibitors not selectively and irreversibly blocked both MAO isoforms this led to side-effects such as hypertensive crisis (also called "chese syndrome") especially due to MAO-A inhibition, that blocking tyramine metabolism trigger a cascade in which excessive amounts of norepinephrine can lead to a hypertensive crisis. Second generation MAO-A reversible inhibitors such as moclobemide and brofaromin displayed in clinical trials potent antidepressant activity but a negligible propensity to induce after ingestion of tyramine, hypertensive crisis at the therapeutic dosage (Bonnet U., CNS Drug review, 2003, 9, 1, 97-140). This because reversibility allows competition and thus ingested tyramine is able to displace the inhibitor from the enzyme. MAO-B selective reversible inhibitors do not give rise to hypertensive crisis. Recent studies provide evidence that also anxiety disorders may be linked to malfunction in serotonine neurotransmission and unbalances in catecholamine metabolism. Efficacy of MAO inhibitors in the treatment of anxiety disorders has been demonstrated by several clinical trials and case reports (J. Clin. Psychiatry, 2006, 67, S12:20-26). Inhibitors of MAO-B prolong the activity of both endogenously and exogenously derived dopamine, making them an option either as monotherapy in early Parkinson's disease (PD) or as add-on therapy in patients treated with levodopa. Efficacy of the MAO-B approach for the PD treatment was clinically proved by trials involving the two US approved MAO-B inhibitors Rasagiline and Selegiline as well as using Safinamide, at the present in phase III. All these drugs provided symptomatic relief when used as monotherapy or as adjunctive therapy, even displaying potential as disease-modifying agents.

Imidazoline receptors, a family of non-adrenergic receptors, first identified by Bousquet in 1984, are widely distributed both centrally and peripherally. Three main subclasses of imidazoline binding sites (IBS) have been identified: $I_1$-IBS, which preferentially binds clonidine, is located on the membrane of neurones and is involved in the central blood pressure regulation, $I_2$-IBS, which preferentially binds idazoxan, is located principally in the outer membrane of mitochondria, and $I_3$-IBS that has been identified in the pancreas. Protein isolation studies have shown that MAO-A and MAO-B are both $I_2$ binding proteins. Further pharmacological studies demonstrated how agonists at $I_2$-IBS are able to inhibit MAO activity thus providing an alternate approach to MAO inhibitors for controlling the activity of both MAO-A and MAO-B. It was shown in several animal models how $I_2$-IBS ligands are able to modulate central monoamine levels, as well as it has been recently shown how alterations in $I_2$-IBS density can be highlighted in depressed patients. Agmantine is an endogenous amine, formed by arginine decarboxylation, which has been proposed as a neurotransmitter in the CNS. Recently for Agmantine and other selective $I_2$-IBS agonists such as 2-BFI (2-benzofuranylimidazoline) and norharman (β-carboline) antidepressant properties in several animal models have been reported, thus confirming in vivo that $I_2$-imidazoline receptor is a new pharmacological target for the treatment of depression and related disorders (M P Zeidan, Eur. J. Pharmacology, 2007, 565, 1-3, 125-31).

Narcotic and alcohol withdrawal is often accompanied by atypical depression which give rise to resumption of alcohol or narcotics, accordingly antidepressant treatment including treatment with MAO inhibitors can generally be considered as a pharmacological approach to treat narcotic and alcohol abuse. However in some cases MAO inhibitors have been proven by preclinical or clinical trials even superior than other anti-depressive drugs for several reasons.

Nicotine induces tollerance and addiction by acting on the central dopaminergic pathways, thus only 50% reduction in nicotine consumptions may trigger withdrawal symptoms such as anxiety, depressive symptoms, cognitive disorders, sleep disorders. The use of MAO inhibitors as a new pharmacotherapy for the treatment of smoking dependence is based upon both the compensation effect of these drugs on the dopaminergic pathway and to the anti-depressive effects that should avoid remission episodes (T. P. George et al., Clin. Pharmacol Ther., 2008, 83, 4, 619-21).

Cocaine abuse is a serious health problem in many areas of the world, up to date there are no approved pharmacological treatments to overcome cocaine dependence. Preclinical studies suggest that cocaine dependence may be due to dopamine transporter inhibition exerted by cocaine, which give rise to a dopamine reinforced effect. MAO inhibitors and particularly MAO-B inhibitors, as proved by preliminary trials with the MAO-B inhibitor selegiline, increasing the monoamine levels can help in overcoming cocaine dependence counteracting the dopamine level drop due to the drug withdrawal (E. J. Houtsmeller, Psychopharmacology, Berl., 2004, 172, 1, 31-40).

Preclinical models highlighted how $I_2$-IBS ligands enhances analgesic action of morphine and inhibits tollerance and dependence to opioids (A. Mirales et al., Eur. J. Pharmacology, 2005, 22, 518, 2-3, 234-242). Agmantine and 2-BFI along with other $I_2$-IBS agonists have been shown to potentiate opioid induced analgesia and to attenuate the development of tolerance and dependence, while $I_2$-IBS antagonist such as idazoxan completely reversed these effects. Interestingly, the same effects of potentiation of morphine analgesia and prevention of tollerance and dependence was observed in animal models also with MAO inhibitors (A Wasik et al., J. Physiol. Pharmacol., 2007, 58, 2, 235-52; K Grasing et al., Behav Pharmacol., 2005, 16, 1, 1-13), and confirmed clinically for Moclobemide, a reversible MAO-A inhibitor (G. Vaiva, Prog. Neuropsychopharmacol Biol. Psychiatry, 2002, 26, 3, 609-11).

DESCRIPTION OF THE INVENTION

In our previous patent application WO2008/014822 we described 2-aryl- and 2-hetroaryl-6-(1H-imidazo-1-yl)-quinazoline and quinoline derivatives for the treatment of pain and inflammatory disorders. More recently we have discovered that 2-aryl- and 2-hetroaryl-6-(1H-imidazo-1-yl)-quinazoline and quinoline derivatives of formula (I) are surprisingly endowed with outstanding MAO inhibitory properties and are potent $I_2$-IBS agonists. Accordingly, the present invention is directed to the use of compounds of formula (I), their pharmaceutically acceptable salts and/or solvates, and corresponding pharmaceutical compositions, for the pharmacological treatment of Depression including Major depressive disorder, Dysthymic disorder, Type II bipolar disorder, manic depression, Anxiety disorders including post-traumatic stress disorder, panic disorder.

According to the rational reported in the background, this invention is further directed to the use of compounds of formula (I), their pharmaceutically acceptable salts and/or solvates, and corresponding pharmaceutical compositions, for the pharmacological treatment of Parkinson's disease. In another embodiment this invention is directed to the use of compounds of formula (I), their pharmaceutically acceptable salts and/or solvates, and pharmaceutical compositions thereof, for the pharmacological treatment of the withdrawal symptoms and to avoid remission episodes for alcohol, tobacco and narcotics abuse including Cocaine abuse. In another embodiment this invention is directed to the use of compounds of formula (I), their pharmaceutically acceptable salts and/or solvates, and corresponding pharmaceutical compositions, where compounds of formula (I) are used alone or in combination with morphine or other opioid drugs for potentiation of the opioid pharmacological action and/or for the dosage reduction of the opioid drug. In another embodiment this invention is directed to the use of compounds of formula (I), their pharmaceutically acceptable salts and/or solvates, and pharmaceutical compositions thereof, for the treatment of tolerance and dependence due to opioid drugs use.

Compounds of Formula (I):

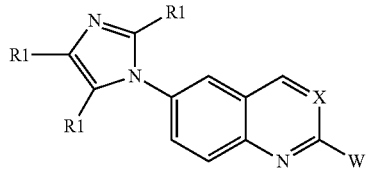

wherein:
X is independently selected from —CH group or a nitrogen atom (—N);
W is independently selected from an aryl group, an heteroaryl group, or an heteroaryl group of formula II:

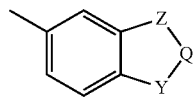

Heteroaryl group of formula II when W is an aryl group, it is intended an unsubstituted or substituted phenyl, with one or more substituents independently selected from halogen (—F, —Cl, —Br), trifluoromethyl (—$CF_3$), alkyl (—$R_2$), hydroxyl (—OH), alkoxy (—$OR_2$), trifluoromethoxy (—$OCF_3$), cyano (—CN), carboxamido (—$CONHR_3$ or —$NHCOR_3$ or —$CONR_2R_3$ or —$NR_2COR_3$), carbonyl (—CO—$R_3$), alkylthio or thiol (—$SR_3$), sulfinyl (—$SOR_3$) and sulfonyl (—$SO_2R_3$) being $R_2$ and $R_3$ as defined below;
when W is an heteroaryl group it is independently selected between the following penta- or hexa-atomic heterocycles: 2-furyl, 3-furyl, 2-thienyl, 3-thienyl, pyrrole-2-yl, pyrrole-3-yl, pyridine-4-yl, pyridine-3-yl, pyrimidin-4-yl. The heterocyclic ring can be substituted with one or two substituents independently selected from: $R_1$, alkoxy (—$OR_2$) or hydroxy (—OH), being $R_1$ and $R_2$ as defined below;
when W is an heteroaryl group of formula (II), it is a benzocondensed-5 or -6 membered heterocycle, wherein:
Z and Y are independently selected from: an oxygen atom (—O—), a sulphur atom (—S—), or the groups: —$CHR_3$—, —$CR_3$=, —NH—, —N=;
Q is independently selected from the groups: —$CHR_3$—, —CH=, —$CR_3$=, —$CHR_3$—$CH_2$—; provided that the combination of Y, Z, Q groups give rise to: 1,3-benzodioxole, benzofuran, 2,3-dihydrobenzofuran, benzothiophene, 2,3-dihydrobenzothiophene, indole, 2,3-dihydroindole, benzimidazole, benzoxazole, benzothiazole, 2H-3,4-dihydrobenzopyran, [1,4]-benzodioxine, 2,3-dihydro-[1,4]-benzodioxine (1,4-benzodioxan);
$R_1$ is independently selected from hydrogen (—H), $C_1$-$C_4$ alkyl, hydroxymethyl (—$CH_2OH$), aminomethyl (—$CH_2NH_2$), alkylaminomethyl [$CH_2NH(R_2)$], or di-alkylaminomethyl [$CH_2N(R_2)_2$]trifluoromethyl (—$CF_3$). The $C_1$-$C_4$ alkyl group is a linear or branched saturated or unsaturated $C_1$-$C_4$ hydrocarbon chain. Provided that in compounds of formula (I) not more than two $R_1$ groups substituting the imidazole ring, are simultaneously $C_1$-$C_4$ alkyl or trifluoromethyl (—$CF_3$) and only one $R_1$ group is hydroxymethyl (—$CH_2OH$), aminomethyl (—$CH_2NH_2$), alkylaminomethyl [$CH_2NH(R_2)$], or di-alkylaminomethyl [$CH_2N(R_2)_2$];
$R_2$ is a $C_1$-$C_6$ alkyl chain. Herein the $C_1$-$C_6$ alkyl chain is intended as above defined for $C_1$-$C_4$ chain but optionally substituted with an aryl, aryl being herein as defined above;
$R_3$ is independently selected from hydrogen, $C_1$-$C_4$ alkyl as defined above for $R_1$.

Compounds of formula (I) as defined above have tautomers, the scope of the present invention includes all the possible tautomers of compounds of formula (I).

Compounds of formula (I) as defined above, when W is an aryl or an heteroaryl of formula (I) are encompassed within the compounds of formula (I) of our previous application WO2008/014822, however some of them are novel compounds, not previously described in the examples of our patent application WO2008/014822.

In a further embodiment this invention is directed to these novel compounds, their pharmaceutically acceptable salts and solvates, the corresponding pharmaceutical compositions, and their use for the pharmacological treatment of those diseases as above detailed for compounds of formula (I).

These novel compounds are:
[6-(2-methyl-1H-imidazol-1-yl)-2-phenyl]quinazoline.
[6-(2-methyl-1H-imidazol-1-yl)-2-(4-methoxyphenyl)] quinazoline
[6-(4-methyl-1H-imidazol-1-yl)-2-phenyl]quinazoline.
[6-(5-methyl-1H-imidazol-1-yl)-2-phenyl]quinazoline.
[6-(4-methyl-1H-imidazol-1-yl)-2-(4-methoxyphenyl)] quinazoline.
[6-(4-methyl-1H-imidazol-1-yl)-2-(3-methoxyphenyl)] quinazoline.
[6-(4-methyl-1H-imidazol-1-yl)-2-(2-methoxyphenyl)] quinazoline.
[6-(4-1H-imidazol-1-yl)-2-(1,3-benzodioxol-5-yl)]quinazoline.
[6-(4-methyl-1H-imidazol-1-yl)-2-(4-fluorophenyl)] quinazoline.
[6-(4-methyl-1H-imidazol-1-yl)-2-(4-metanesulfonylphenyl)]quinazoline.
[6-(1H-imidazol-1-yl)-2-(4-methoxyphenyl)]quinoline.
[6-(1H-imidazol-1-yl)-2-(2-methoxyphenyl)]quinoline.
[6-(1H-imidazol-1-yl)-2-(1,3-benzodioxol-5-yl)]quinoline.
[6-(1H-imidazol-1-yl)-2-(4-fluorophenyl)]quinoline.
[6-(1H-imidazol-1-yl)-2-(4-dimethylaminophenyl)]quinoline
[6-(1H-imidazol-1-yl)-2-(4-trifluoromethoxyphenyl)]quinoline.
[6-(1H-imidazol-1-yl)-2-(2-methyl-4-trifluoromethoxyphenyl)]quinoline.
[6-(1H-imidazol-1-yl)-2-(4-dimethylaminophenyl)]quinoline.
[6-(1H-imidazol-1-yl)-2-(4-methansulfonylphenyl)]quinoline.
[6-(2-methyl-1H-imidazol-1-yl)-2-(4-methoxyphenyl)] quinoline.
[6-(2-methyl-1H-imidazol-1-yl)-2-(2-methoxyphenyl)] quinoline.
[6-(4-methyl-1H-imidazol-1-yl)-2-phenyl)]quinoline.
[6-(4-methyl-1H-imidazol-1-yl)-2-(4-methoxyphenyl)] quinoline.
[6-(4-methyl-1H-imidazol-1-yl)-2-(4-fluorophenyl)]quinoline.

[6-(4-methyl-1H-imidazol-1-yl)-2-(4-methylthiophenyl)]quinoline.

Compounds of formula (I) as defined above, when W is an heteroaryl as above defined, are not encompassed within the compounds of formula (I) of our previous application WO2008/014822.

In a further embodiment this invention is directed to these novel compounds of formula (I) where W is a heteroaryl as above defined, their pharmaceutically acceptable salts and solvates, the corresponding pharmaceutical composition, and their use for the pharmacological treatment of those diseases as detailed for compounds of formula (I).

According to this invention the compounds of formula (I) may be used as the free base, as a pharmaceutically acceptable salt, or as a solvate or hydrate form. The salts of compounds of formula (I) are pharmaceutically acceptable addition salts with inorganic and organic acids. Representative not limiting examples of inorganic salts of compounds of formula (I) are: hydrochloride, hydrogensulphate, sulphate, hydrogenphosphate and phosphate. Corresponding representative not limiting examples of organic salts are: methanesulfonate, maleate, succinate, fumarate, tartrate, malonate and oxalate.

Methods for the preparation of compounds of formula (I) are widely described in our previous application WO2008/014822, however especially for those compounds of formula (I) where the imidazolyl group is substituted ($R_1$ is not hydrogen), very low yields and complex reaction mixtures are often obtained when the methods for the preparation of compounds of formula (I) reported in WO2008/014822 are used. In another embodiment this invention provides new, more practical and valuable methods for preparing compounds of formula (I), characterized by higher average yields and simpler procedures for the isolation and purification of the product.

In another embodiment this invention provides pharmaceutical compositions for compounds of formula (I) useful for the pharmacological treatment of those diseases as above detailed. Within the scope of the present invention the term pharmaceutical composition (drug product) refers to any oral or parenteral dosage form, suitable for the treatment of the above pathologies, that contains an effective amount of at least one of the active pharmaceutical ingredients (drug substances), compounds of formula (I), its salts or solvates thereof, and a pharmaceutically acceptable carrier, excipients or diluents as defined below, for oral or parenteral administration.

Representative not limiting examples of compounds of formula (I) are listed in Table 1.

TABLE 1

| Name | Structure | MW | Example |
|---|---|---|---|
| [6-(1H-imidazol-1-yl)-2-phenyl-]quinazoline. | 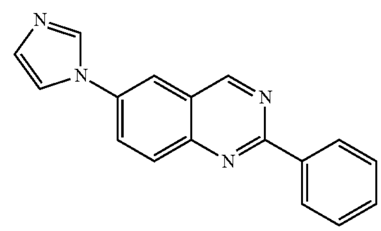 | 272.31 | 1 |
| [6-(2-methyl-1H-imidazol-1-yl)-2-phenyl)-]quinazoline. | 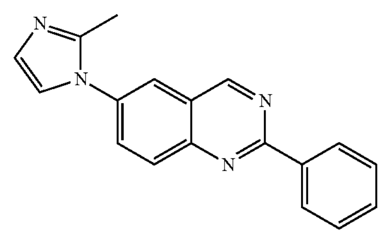 [SMILES: Cc1nccn1-c1ccc2nc(-c3ccccc3)ncc2c1] | 286.34 | 2 |
| [6-(2-methyl-1H-imidazol-1-yl)-2-(4-methoxyphenyl)-]quinazoline. | 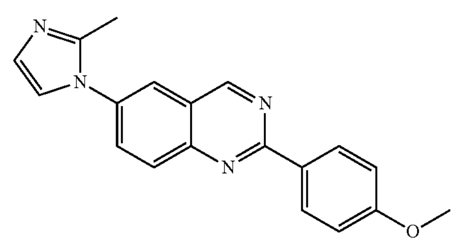 [SMILES: COc1ccc(-c2ncc3cc(-n4ccnc4C)ccc3n2)cc1] | 316.37 | 3 |
| [6-(4-methyl-1H-imidazol-1-yl)-2-phenyl]quinazoline. | 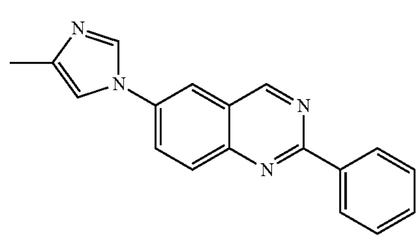 [SMILES: Cc1cn(-c2ccc3nc(-c4ccccc4)ncc3c2)cn1] | 286.34 | 4 |

TABLE 1-continued

| Name | Structure | MW | Example |
|---|---|---|---|
| [6-(5-methyl-1H-imidazol-1-yl)-2-phenyl)]quinazoline. | 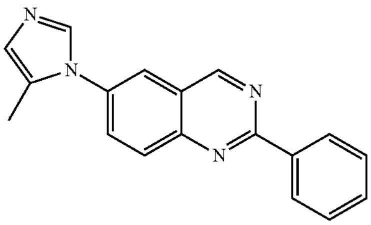 [SMILES: Cc1cncn1-c1ccc2nc(-c3ccccc3)ncc2c1] | 286.34 | 5 |
| [6-(4-methyl-1H-imidazol-1-yl)-2-(4-methoxyphenyl)]-quinazoline. | 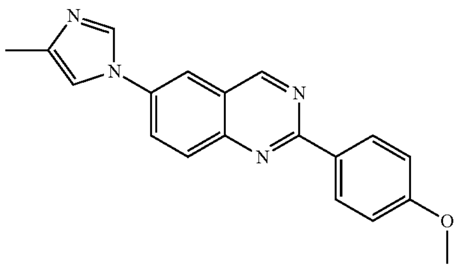 | 316.37 | 6 |
| [6-(4-methyl-1H-imidazol-1-yl)-2-(2-methoxyphenyl)-]quinazoline. | 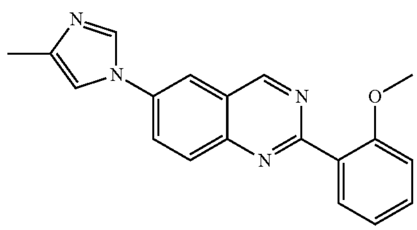 | 316.37 | 7 |
| [6-(4-methyl-1H-imidazol-1-yl)-2-(3-methoxyphenyl)-]quinazoline. | 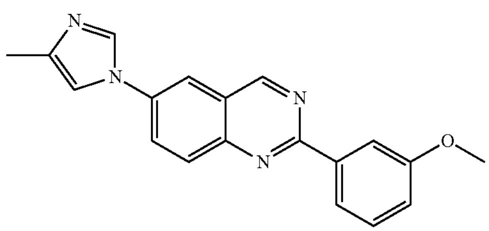 | 316.37 | 8 |
| [6-(4-methyl-1H-imidazol-1-yl)-2-(1,3-benzodioxol-5-yl)-]quinazoline. | 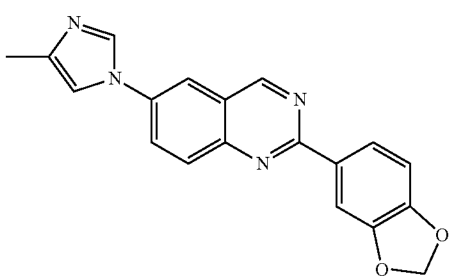 [SMILES: Cc1cn(-c2ccc3nc(-c4ccc5c(c4)OCO5)ncc3c2)cn1] | 330.35 | 9 |
| [6-(4-methyl-1H-imidazol-1-yl)-2-(4-fluorophenyl)-]quinazoline. | 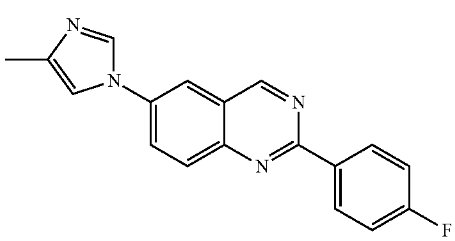 [SMILES: Cc1cn(-c2ccc3nc(-c4ccc(F)cc4)ncc3c2)cn1] | 304.33 | 10 |

TABLE 1-continued

| Name | Structure | MW | Example |
|---|---|---|---|
| [6-(4-methyl-1H-imidazol-1-yl)-2-(4-methanesulfonylphenyl)]-quinazoline. | 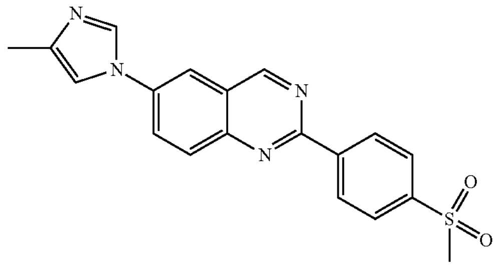 [SMILES: Cc1cn(-c2ccc3nc(-c4ccc(S(C)(=O)=O)cc4)ncc3c2)cn1] | 364.43 | 11 |
| [6-(4-methyl-1H-imidazol-1-yl)-2-(3-furyl)]-quinazoline. | 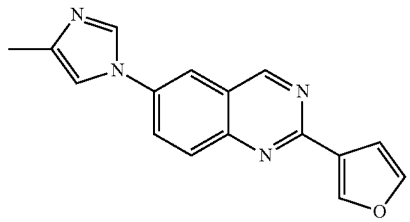 [SMILES: Cc1cn(-c2ccc3nc(-c4ccoc4)ncc3c2)cn1] | 276.30 | 12 |
| [6-(1H-imidazol-1-yl)-2-(1,3-benzodioxol-5-yl)-]quinazoline. | 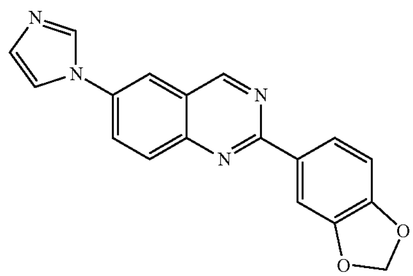 [SMILES: c1cn(-c2ccc3nc(-c4ccc5c(c4)OCO5)ncc3c2)cn1] | 316.32 | 13 |
| [6-(1H-imidazol-1-yl)-2-(benzofuran-5-yl)]quinazoline dihydrochloride trihydrate. | 2•HCl•3H$_2$O | 439.30 | 14 |
| [6-(1H-imidazol-1-yl)-2-(2,3-dihydro-1,4-benzodioxin-6-yl)]quinazoline. | 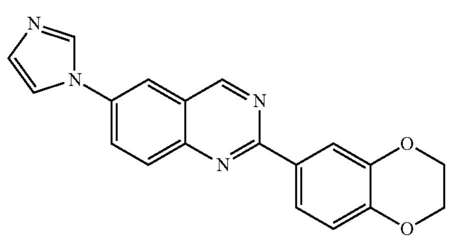 [SMILES: c1cn(-c2ccc3nc(-c4ccc5c(c4)OCCO5)ncc3c2)cn1] | 330.35 | 15 |
| [6-(1H-imidazol-1-yl)-2-(1,3-benzodioxol-5-yl)]quinoline dihydrochloride. | •2HCl | 351.79 | 16 |

TABLE 1-continued

| Name | Structure | MW | Example |
|---|---|---|---|
| [6-(1H-imidazol-1-yl)-2-phenyl-]quinoline. | | 271.32 | 17 |
| [6-(1H-imidazol-1-yl)-2-(4-methoxypheny)]quinoline dihydrochloride. | •2HCl | 374.27 | 18 |
| [6-(1H-imidazol-1-yl)-2-(2-methoxypheny)]quinoline dihydrochloride. | •2HCl | 374.27 | 19 |
| [6-(1H-imidazol-1-yl)-2-(3-furyl]quinoline dihydrochloride. | •2HCl | 334.20 | 20 |
| [6-(1H-imidazol-1-yl)-2-(4-fluoropheny)]quinoline dihydrochloride. | •2HCl | 362.31 | 21 |
| [6-(1H-imidazol-1-yl)-2-(4-dimethylaminopheny)]quinoline trihydrochloride. | •3HCl | 423.77 | 22 |

TABLE 1-continued

| Name | Structure | MW | Example |
|---|---|---|---|
| [6-(1H-imidazol-1-yl)-2-(4-trifluoromethoxypheny)]quinoline dihydrochloride | 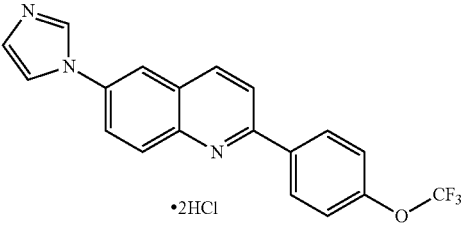 [SMILES: FC(F)(F)Oc1ccc(-c2ccc3cc(-n4ccnc4)ccc3n2)cc1 ; "·2HCl"] | 428.24 | 23 |
| [6-(1H-imidazol-1-yl)-2-(2-methyl)-4-trifluoromethoxypheny)]quinoline dihydrochloride | 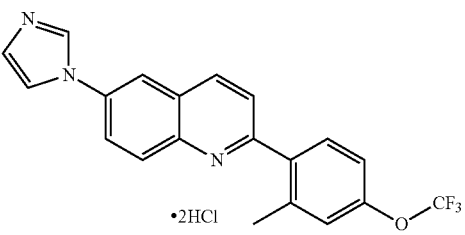 [SMILES: Cc1cc(OC(F)(F)F)ccc1-c1ccc2cc(-n3ccnc3)ccc2n1 ; "·2HCl"] | 442.27 | 24 |
| [6-(1H-imidazol-1-yl)-2-(4-methansulfonylpheny)]quinoline dihydrochloride | 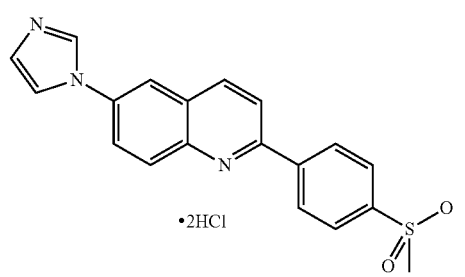 | 422.33 | 25 |
| [6-(2-methyl-1H-imidazol-1-yl)-2-(4-methoxypheny)]quinoline dihydrochloride | 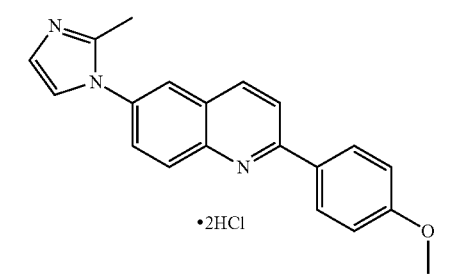 [SMILES: COc1ccc(-c2ccc3cc(-n4ccnc4C)ccc3n2)cc1 ; "·2HCl"] | 388.38 | 26 |
| [6-(2-methyl-1H-imidazol-1-yl)-2-(2-methoxypheny)]quinoline dihydrochloride | 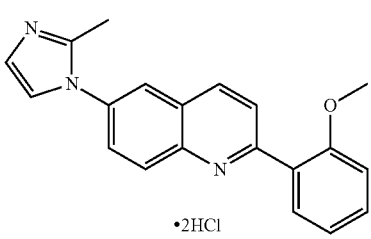 [SMILES: COc1ccccc1-c1ccc2cc(-n3ccnc3C)ccc2n1 ; "·2HCl"] | 388.38 | 27 |
| [6-(4-methyl-1H-imidazol-1-yl)-2-(furan-3-yl)-]quinoline dihydrochloride | 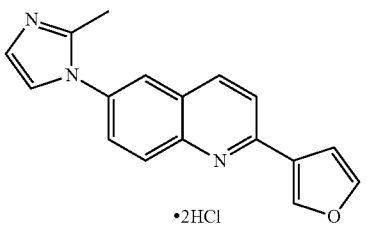 [SMILES: Cc1nccn1-c1ccc2nc(-c3ccoc3)ccc2c1 ; "·2HCl"] | 348.31 | 28 |

TABLE 1-continued

| Name | Structure | MW | Example |
|---|---|---|---|
| [6-(2-methyl-1H-imidazol-1-yl)-2-(pheny)]quinoline dihydrochloride | •2HCl | 358.35 | 29 |
| [6-(4-methyl-1H-imidazol-1-yl)-2-phenyl]-quinoline dihydrochloride | •2HCl | 285.35 | 30 |
| [6-(4-methyl-1H-imidazol-1-yl)-2-(4-methoxypheny)]quinoline dihydrochloride | •2HCl | 388.38 | 31 |
| [6-(4-methyl-1H-imidazol-1-yl)-2-(4-fluoropheny)]quinoline dihydrochloride | •2HCl | 376.34 | 32 |
| [6-(4-methyl-1H-imidazol-1-yl)-2-(4-methylthiopheny)]quinoline dihydrochloride | •2HCl | 404.34 | 33 |

Preparation of the Compounds of the Invention

Compounds of formula (I) can be prepared, as described in WO2008/014822, by reacting a compound of formula (III) with an imidazole derivative of formula (IV) as depicted in Scheme 1, wherein X, W and $R_1$ have the same meanings as defined above for compounds of formula (I), and Hal is an halogen atom such as fluorine, chlorine, bromine and iodine, typically fluorine or bromine.

Scheme 1:

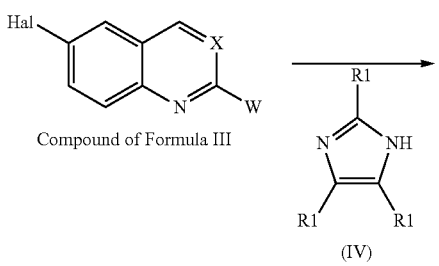

-continued

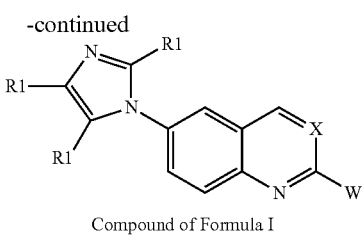

Compound of Formula I

The reaction of a compound of formula (III) can be carried out using an imidazole derivative of formula (IV) either as free base or its alkaline metal salt (sodium, lithium or potassium salt), according to the general reaction conditions described in WO2008/014822, or more in particular using CuI or Cu$_2$O as catalyst, dimethylethylendiamine or 4,7-dimethoxy-1,10-phenantroline as ligands, and diglyme as solvent, caesium carbonate as base, at a temperature of about 150° C. for 20-50 hours.

When X is a nitrogen atom, compounds of formula (III) can be prepared from known diamines of formula (V) as depicted in Scheme 2.

Scheme 2:

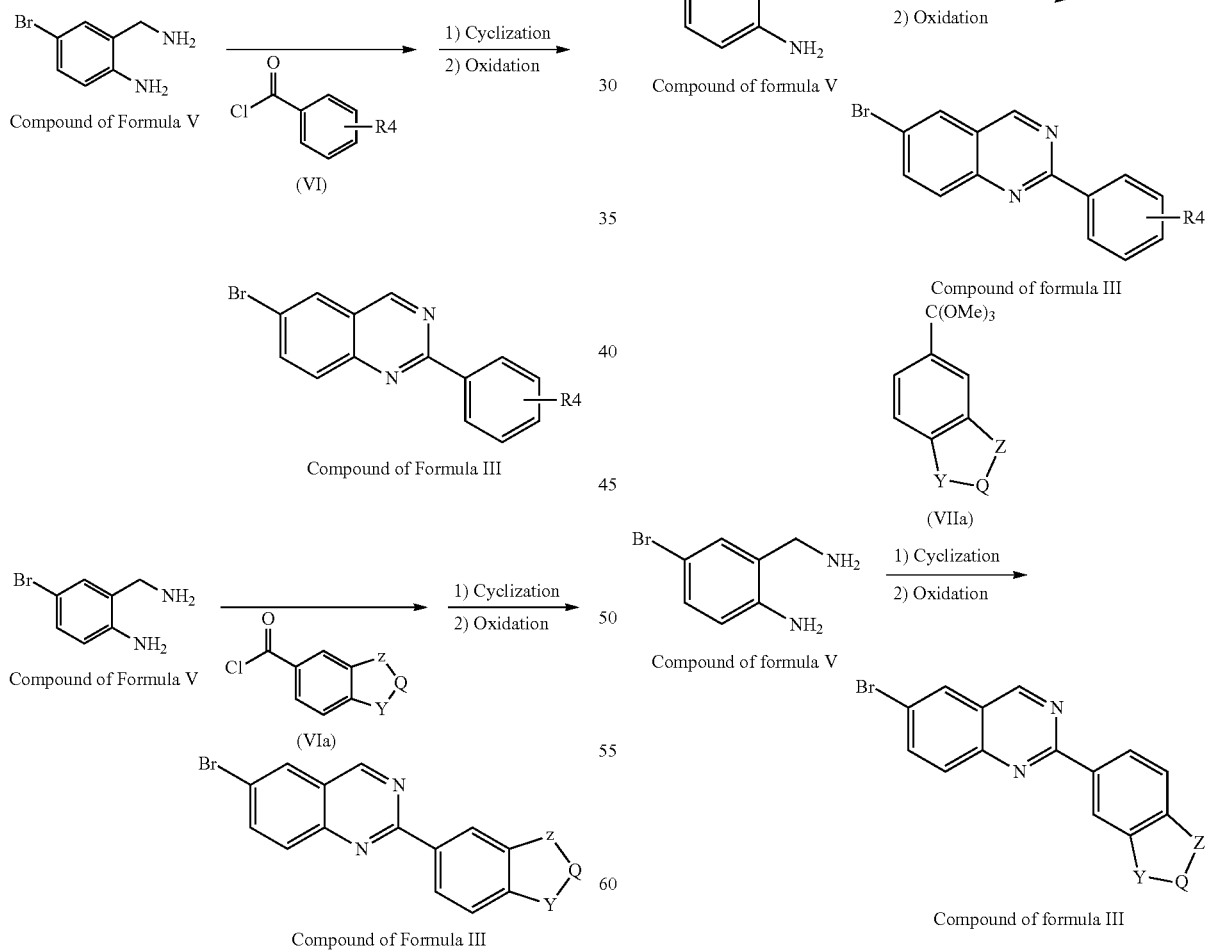

Where Y, Q and Z have the same meanings as for compounds of formula (I), and R$_4$ is any of the substituents above reported as substituents for the aryl group in compounds of formula (I). Compounds of formula (V) are prepared according to known methods, compounds of formula (VI) and (VIa) are known compounds, or are prepared according to known methods. Reaction conditions as previously described in WO2008/014822 for the cyclization and oxidation steps can be used, however higher yields can be obtained for the most of cases using the reaction conditions reported in Example 1. This improved synthetic procedure also consists of simpler operations, thus giving rise to a more practical synthetic process.

Alternatively, a compound of formula (III) where X is a nitrogen atom (—N) can be prepared by cyclization of the diamine of formula (V) with an orthoester of formula (VII) or (VIIa) as reported in scheme 3.

Scheme 3:

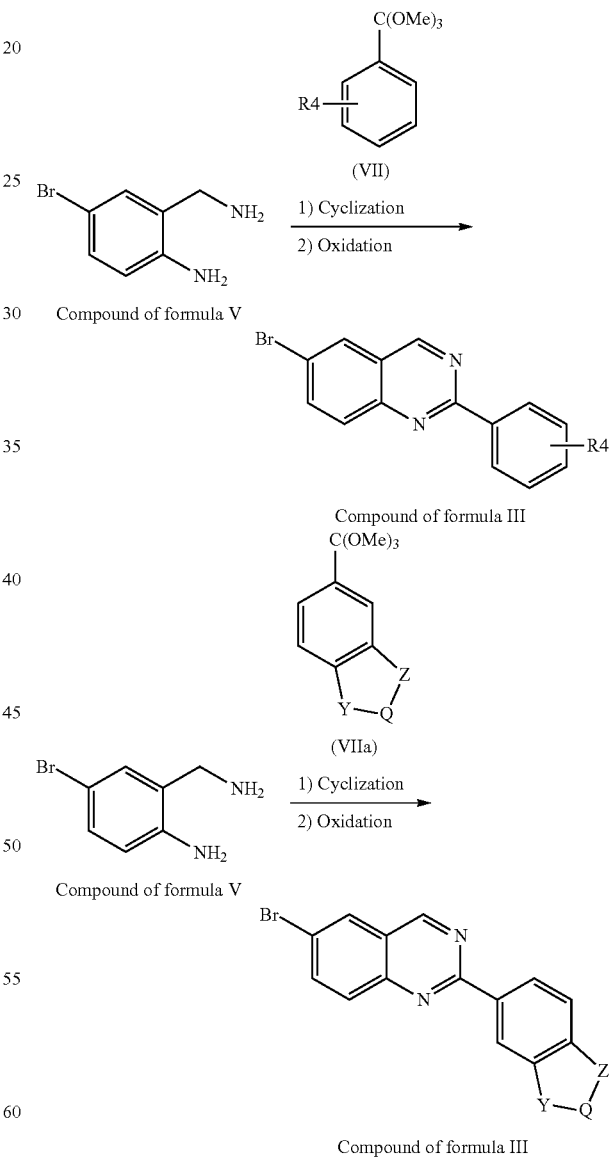

Wherein R$_4$, Y, Q and Z are as above described. The cyclization reaction of the orthoesters of formula (VII) and (VIIa) with the bisamines of formula (V) is carried out in toluene or another inert organic solvent, using acid catalysis, typically p-toluene sulfonic acid, at the reflux temperature for about 50 hrs. The oxidation step can be carried out using MnO$_2$ in dichloromethane.

Alternatively, compounds of formula (I) where X is a nitrogen atom (—N) can be prepared by cyclization of diamine of formula (VIII) with Pinner salts of formula (IX) or (IXa) as reported in Scheme 4.

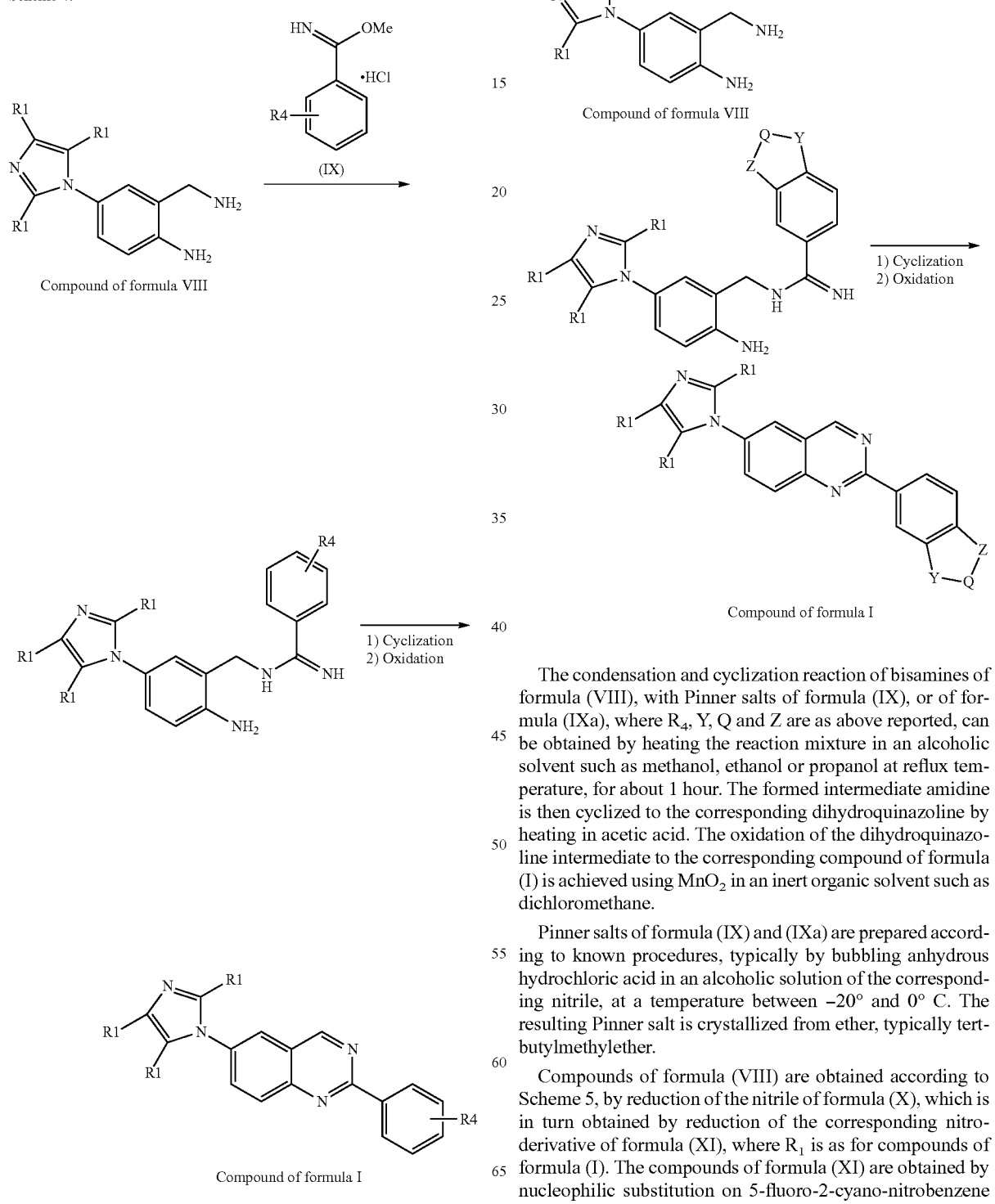

The condensation and cyclization reaction of bisamines of formula (VIII), with Pinner salts of formula (IX), or of formula (IXa), where R$_4$, Y, Q and Z are as above reported, can be obtained by heating the reaction mixture in an alcoholic solvent such as methanol, ethanol or propanol at reflux temperature, for about 1 hour. The formed intermediate amidine is then cyclized to the corresponding dihydroquinazoline by heating in acetic acid. The oxidation of the dihydroquinazoline intermediate to the corresponding compound of formula (I) is achieved using MnO$_2$ in an inert organic solvent such as dichloromethane.

Pinner salts of formula (IX) and (IXa) are prepared according to known procedures, typically by bubbling anhydrous hydrochloric acid in an alcoholic solution of the corresponding nitrile, at a temperature between −20° and 0° C. The resulting Pinner salt is crystallized from ether, typically tert-butylmethylether.

Compounds of formula (VIII) are obtained according to Scheme 5, by reduction of the nitrile of formula (X), which is in turn obtained by reduction of the corresponding nitro-derivative of formula (XI), where R$_1$ is as for compounds of formula (I). The compounds of formula (XI) are obtained by nucleophilic substitution on 5-fluoro-2-cyano-nitrobenzene with the imidazolyl derivative of formula (IV).

Scheme 5:

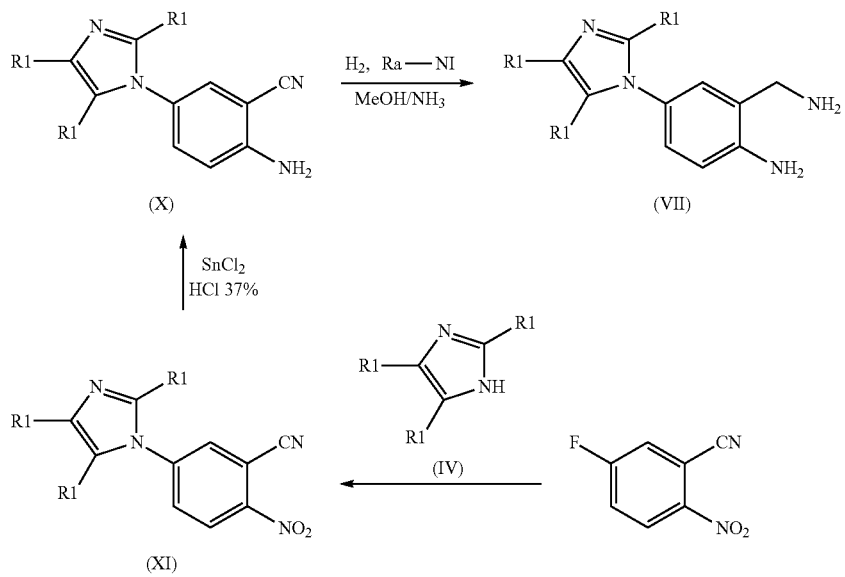

Catalytical reduction of a compound of formula (X) to provide a compound of formula (VII) can be accomplished using Nickel-Raney as catalyst, at an hydrogen pressure of about 60 bar, in methanol or ethanol containing about 10% of ammonia (gas), at a temperature of 30-60° C. Conversion of a cyano-derivative of formula (XI) into a compound of formula (X) can be obtained using $SnCl_2$ in concentrated HCl at a temperature ranging between −10° and 0°. Derivatives of formula (XI) are obtained by reaction of 5-fluoro-2-cyano-nitrobenzene with the imidazolyl derivatives of formula (IV), in an organic solvent, typically acetonitrile, at a temperature of 50-90° C. When the $R_1$ substituent in the compound of formula (IV) is in position −4 and the $R_1$ substituents in the other positions are hydrogen, regioisomers of compounds of formula (XI) could be obtained. These regioisomers can be separated by column chromatography and/or crystallization.

Compounds of formula (I) where X is a —CH group, can be prepared from a compound of formula (XII) by reaction with a boronate of formula (XIII) or (XIIIa) as reported in Scheme 6.

Scheme 6:

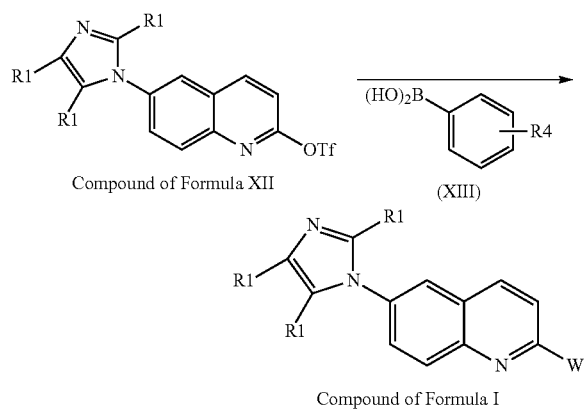

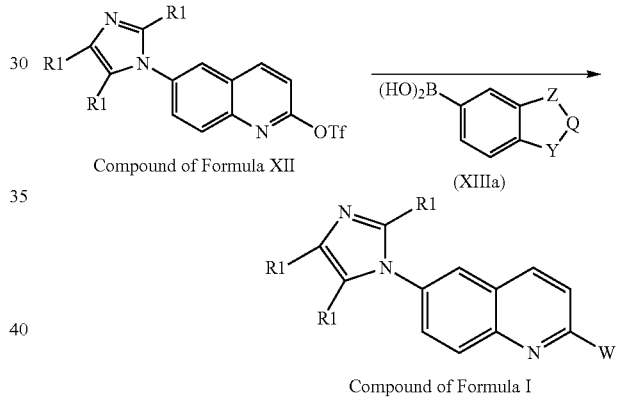

OTf = trifluoromethansulfonate

Wherein $R_1$, $R_4$, W, Y, Z and Q are as above defined. A similar approach which utilizes the Suzuky coupling for preparing compounds of formula (I) as herein defined, but starting from 2-chloro-6-imidazolyl-quinoline derivatives was previously reported in our patent application WO2008/014822. However, the use of the triflate group instead of a chloro atom as previously reported, remarkably increases coupling yields, as well as are higher the yields for the preparation of compounds of formula (XII) in comparison with the corresponding 2-chloroderivatives. The reaction of a compound of formula (XII) with the boronate of formula (XIII) or (XIIIa) is carried out in an inert organic solvent such as toluene, dimethoxyethane or tetrahydrofurane, in the presence of a base such as potassium carbonate or caesium carbonate, with palladium catalysis. Palladium tetrakistriphenylphosphine or a palladium salt and an appropriate ligand can be used as catalyst. Compounds of formula (XIII) or (XIIIa) are commercially available compounds or can be prepared according to methods well known in the art.

Alternatively, compounds of formula (I) can be obtained by reacting compounds of formula (XII) with aryl halides, typically aryl bromides, derivatives of formula (XIIIb) and (XIIIc), according to the Stille reaction (Tetrahedron Letters, 36, 50, 9085, 1995) as depicted in Scheme 6a.

Scheme 6a:

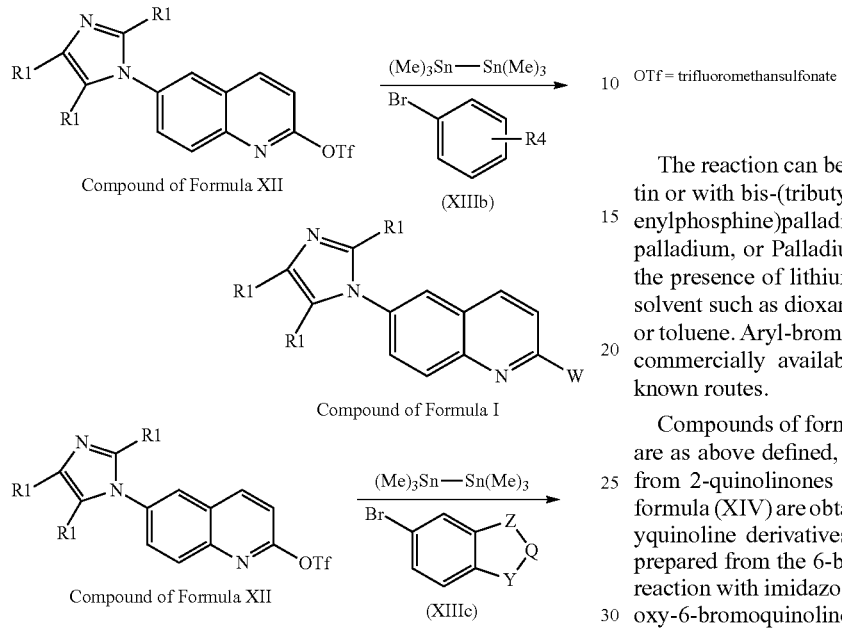

OTf = trifluoromethansulfonate

The reaction can be carried out either with bis-(trimethyl) tin or with bis-(tributyl)tin, using as catalyst: Tetrakis(triphenylphosphine)palladium, or Tris(dibenzylideneacetone)dipalladium, or Palladium-dichlorobis(triphenylphosphine, in the presence of lithium chloride or potassium fluoride, in a solvent such as dioxane, tetrahydrofurane, dimethoxyethane or toluene. Aryl-bromides of formula (XIIIb) and (XIIIc) are commercially available or can be prepared according to known routes.

Compounds of formula (XII) where $R_1$, $R_4$, W, Y, Z and Q are as above defined, are obtained as outlined in scheme 7, from 2-quinolinones of formula (XIV). 2-Quinolinones of formula (XIV) are obtained from the corresponding 2-metoxyquinoline derivatives of formula (XV) which in turn are prepared from the 6-bromo-derivatives of formula (XVI) by reaction with imidazole derivatives of formula (IV). 2-Methoxy-6-bromoquinoline, compound of formula (XVI), is a known compound (RN: 99455-07-7).

Scheme 7:

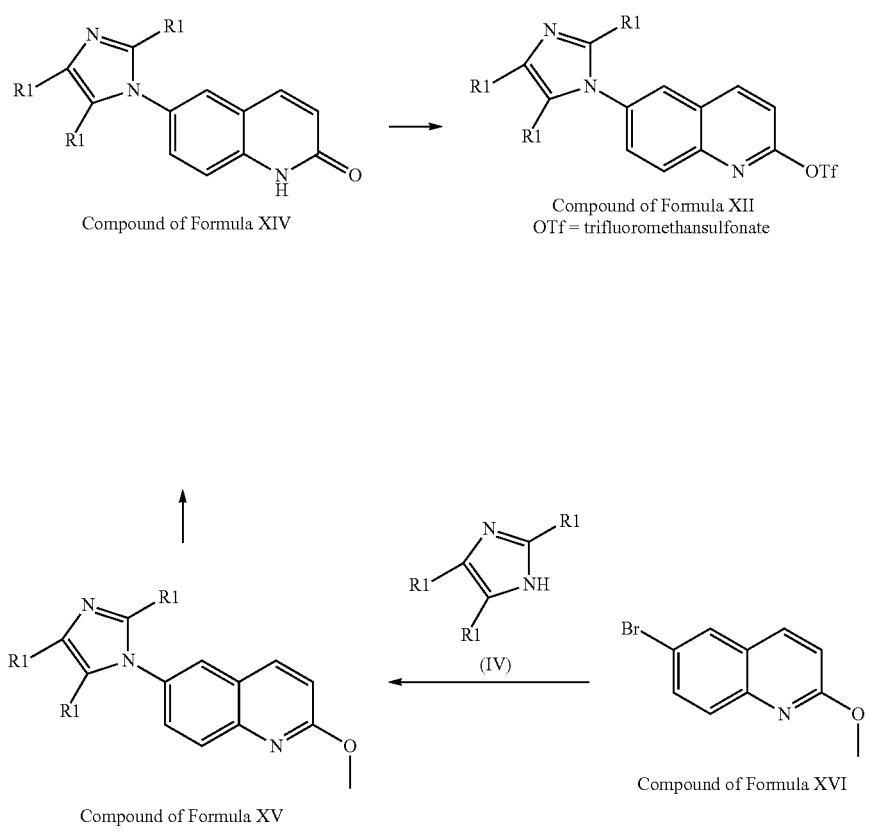

Preparation of a compound of formula (XII) from a compound of formula (XIV) can be carried out in pyridine using trifluoromethanesulfonic anhydride or trifluoromethanesulfonyl chloride at 0°/−10° C., or in dichloromethane using an organic base such as triethylamine or diisopropylethylamine. Alternatively, bis-trifluoromethylanilide in dimethylformamide, using sodium hydride (NaH) as base, can be utilized. Conversion of a compound of formula (XV) into a compound of formula (XIV) is achieved using hydrochloric or hydrobromic acid, at temperatures ranging from 25° C. to reflux temperature. Alternatively, BBr$_3$ in dichloromethane can be used. Compounds of formula (XV) are prepared react- When the imidazole derivative of formula (IV) is substituted (for example R$_1$: methyl, trifluoromethyl, hydroxymethyl), compounds of formula (XIV) can be prepared in high yield by cyclization of a compound of formula (XVII) as depicted in scheme 8. Compounds of formula (XVII) are prepared from anilines of formula (XVIII), which are in turn prepared by reduction of compounds of formula (XIX). Compounds of formula (XIX) are prepared by reacting the commercially available 4-fluoronitrobenzene with imidazoles of formula (IV).

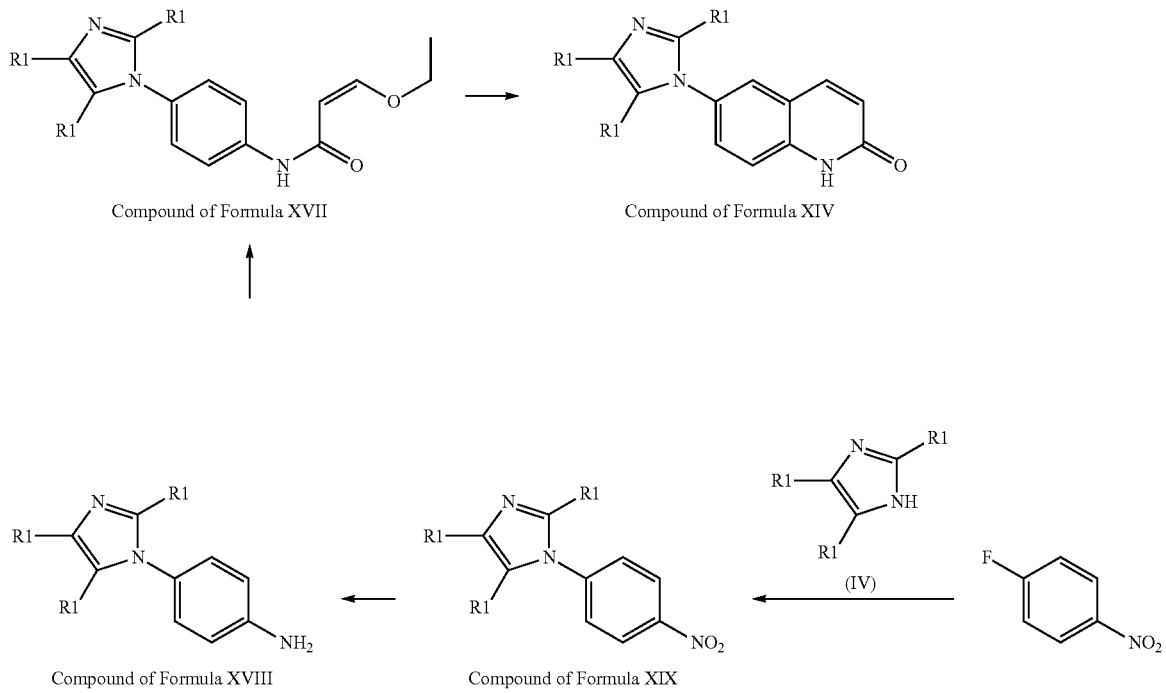

Scheme 8:

ing 6-bromo-2-methoxyquinoline, formula (XVI), with imidazole or substituted imidazoles of formula (IV). The reaction can be carried out using the compounds of formula (IV) as free base or corresponding alkaline metal salt, in the presence of a suitable catalyst, in a solvent such as dimethylformamide (DMF), dimethylsulfoxide (DMSO), acetonitrile, N-methyl-pyrrolidone (NMP), dimethoxyethane, tetrahydrofurane (THF), toluene or xylene, at a temperature ranging from 50° C. to reflux temperature. As catalyst a copper catalyst such as CuI, a mixture of Cu/CuO or Cu(OTf)$_2$.benzene complex can be used, optionally in the presence of ligands such as 8-hydroxyquinoline, 1,10-phenanthroline, dimethylethylenediamine, dibenzylidene acetone. A base such as potassium carbonate, caesium carbonate, triethylammonium carbonate is usually used. Palladium can be also used as catalyst, typically the methodology of Buchwald-Hartwig for imidazole addition to aryl bromides, in DMF as solvent, using both Binap [2,2'-bis(diphenylphosphino)-1,1'-binaphtyl] or Dppf [1,3-bis(diphenylphosphinopropane]palladium soluble catalysts, and potassium tert-butylate as base under microwave heating, can be used for the preparation of compounds of formula (XV).

Cyclization of a compound of formula (XVII) into a compound of formula (XIV) can be obtained by stirring the enolether in a mineral acid (hydrochloric or sulphuric acid), a temperature ranging from −10° C. to +25° C. Alternatively, the cyclization can be carried out in an inert organic solvent, such as dichloromethane, dimethoxyethane or toluene, using a Lewis acid as catalyst. Compounds of formula (XVII) can be prepared by reacting compounds of formula (XVIII) with 3-ethoxyacryloyl chloride in pyridine, or in dichloromethane in the presence of triethylamine. Reduction of compounds of formula (XIX) can be obtained using SnCl$_2$ in an alcohol (ethanol or methanol) or catalytically using hydrogen and Pd/C or PtO$_2$ as catalyst. Compounds of formula (XIX) are obtained from 4-fluoronitrobenzene and the imidazolyl derivatives of formula (IV) according to methods as above described.

Alternatively, a compound of formula (I) where X is either a —CH group or a nitrogen atom (—N) can be prepared from a compound of formula (XX) by reaction with glyoxal or a dicarbonyl derivative of formula (XXI) in the presence of formaldehyde or of an aldehyde of formula R$_1$CHO and ammonium chloride, as summarized in Scheme 9.

Scheme 9:

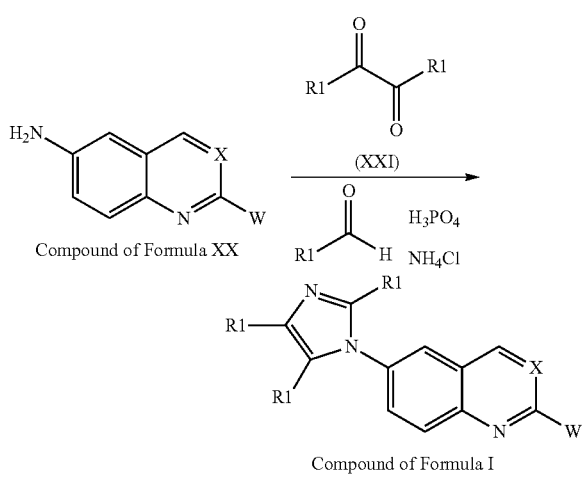

Wherein X, W and R₁ have the same meanings as discussed above for compounds of formula (I).

Compounds of formula (I), where all $R_1$ are hydrogen atoms, can be obtained by treating compounds of formula (XX) with glyoxal, in methanol, typically at room temperature, then adding NH$_4$Cl and formaldehyde, and heating at reflux, finally phosphoric acid is added. Compounds of formula (I) where the imidazole is substituted, can be prepared using a similar procedure but using a dicarbonyl compound of formula (XXI) (wherein at least one R1 is not hydrogen) instead of glyoxal, an aldehyde of formula R$_1$CHO can be used as well (Synthesis, 2003, 2661-2666).

Not limiting representative examples for preparations of compounds of Formula (I) are reported below.

EXAMPLE 1

[6-(1H-imidazol-1-yl)-2-phenyl]quinazoline

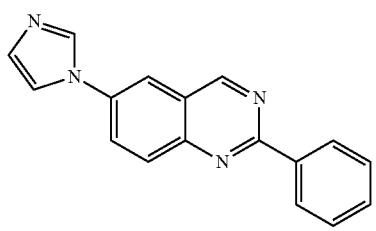 [SMILES: c1ccc(-c2ncc3cc(-n4ccnc4)ccc3n2)cc1]

CuI (6.6 g., 0.034 mol.) and dimethylethylenediamine (8.67 mL, 0.07 mol) were added, under inert atmosphere, to 700 mL of diglyme, at room temperature (r.t.). After stirring few minutes a suspension was obtained, to this suspension 6-bromo-2-phenyl-quinazoline (65.2 g, 0.228 mol.) and imidazole (31.2 g, 0.456 mol., 2 eq.) were added followed by Cs$_2$CO$_3$ (74.7 g., 0.023 mol). The resulting reaction mixture was heated at 150° C., under stirring, for 46 hours. After cooling the reaction mixture was cooled at r.t. and diluted with aqueous saturated NH$_4$Cl solution (3.5 L). Ethyl acetate (AcOEt) was added, the organic phase was separated and the aqueous phase extracted with AcOEt, the collected organic phases were washed with water, filtered, dried and concentrated. The residue dissolved in AcOEt/Methanol (MeOH) (95:5) was filtered through silica gel, concentrated and crystallized from MeOH/hexane to afford the title product (48.7 g, yield 78%). C$_{17}$H$_{12}$N$_4$; MW: 272.31; mp 153.8-158.7° C.; ¹H-NMR (200 MHz, d$_6$-DMSO) 7.23 (s, 1H), 7.58-7.62 (m, 3H), 8.00 (s, 1H), 8.23 (d, 1H), 8.39-8.63 (m, 5H), 9.72 (s, 1H). IR (KBr): 1556, 1506, 1379.

6-bromo-2-phenylquinazoline

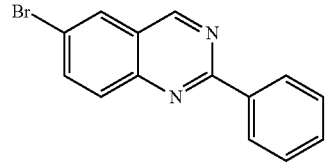 [SMILES: Brc1ccc2nc(-c3ccccc3)ncc2c1]

To dichloromethane (DCM) (3.5 L), 5-bromo-2-aminobenzylamine (137 g, 0.5 mol) and triethylamine (TEA) (250 mL, 1.75 mol) were added at 0° C. on stirring. Then benzoyl chloride (55 mL, 0.45 mol) in DCM (500 mL) was added on stirring at such a rate to keep the temperature at 0-5° C. The mixture was stirred for 3 hours at r.t. Water (1 L) was added and the organic phase was separated, washed with water and dried. The solvent was evaporated and SOCl$_2$ (100 mL) was added to the residue (147.5 g) suspended in toluene (1.5 L). The obtained suspension was heated at reflux for 72 hours. On cooling a precipitate was formed, it was filtered, washed with toluene and suspended in aqueous ammonia, the suspension was extracted with AcOEt. The combined organic phases were washed with water, dried and concentrated to afford the dihydroquinazoline derivative, as a light brown solid (93.8 g., 64% yield). The dihydroquinazoline was dissolved in DCM (2 L) and MnO$_2$ (56.28 g) was added on stirring. The resulting suspension was stirred at r.t. for 18 hours. The suspension was filtered on celite, the cake was washed with DCM and the combined filtrate and washings were concentrated to afford the titled product as an amorphous solid, 85.54 g (60% overall yield; 95% oxidation yield). C$_{14}$H$_9$BrN$_2$; MW: 285.15; MS m/z: 286 (M+1). ¹H-NMR (300 MHz, d$_6$-DMSO) ppm: 7.58-7.61 (m, 3H), 8.02 (d, 1H), 8.17 (dd, 1H), 8.49-8.56 (m, 3H), 9.70 (s, 1H).

6-bromo-2-phenylquinazoline (cyclization using trimethylbenzoic orthoester)

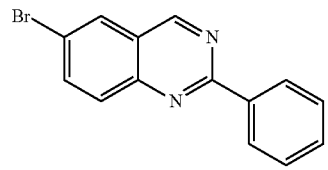 [SMILES: Brc1ccc2nc(-c3ccccc3)ncc2c1]

To toluene (200 mL), 5-bromo-2-amino-benzylamine (9.5 g, 47.2 mmol) and trimethylbenzoic orthoester (8.2 g, 47.2 mmol) were added, followed by p-toulensulfonic acid (1.35 g, 7.1 mmol). The resulting suspension was stirred at reflux for 50 hours. The reaction mixture was cooled at r.t., diluted with AcOEt (150 mL), washed with saturated sodium bicarbonate, then with water. The organic layer was dried and concentrated to provide the intermediate dihydroquinazoline as a light brown solid (8.5 g; 63%). This intermediate is dissolved in DCM (20 mL) at r.t., then MnO$_2$ (5.1 g) was added. The resulting mixture was stirred at r.t. for 48 hrs, then filtered on celite. The filtrate was concentrated to provide the title product as white solid (8.1 g, 95%). $C_{14}H_9BrN_2$; MW: 285.15; MS m/z: 286 (M+1). $^1$H-NMR (300 MHz, $d_6$-DMSO) ppm: 7.58-7.61 (m, 3H), 8.02 (d, 1H), 8.17 (dd, 1H), 8.49-8.56 (m, 3H), 9.70 (s, 1H).

5-bromo-2-amino-benzylamine

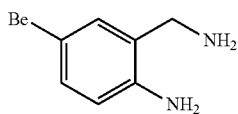

A solution of borane in THF (1 M, 400 ml) was added at 0° C. to a suspension of 5-bromo-anthranilonitrile (60 g, 0.304 mol, prepared as described in S. M. Mackenzie et al, *J. Chem. Soc. C*, 1970, 17, 2298-2308) in THF (450 L), under $N_2$. The mixture was stirred for 72 hours at r.t. After cooling at 0° C. absolute EtOH was added, then HCl was bubbled through the solution. The mixture was concentrated and the residue was suspended in isopropyl ether. The obtained solid was dried to give the di-hydrochloride of the title product (76.6 g, 91.4% yield). $C_7H_9BrN_2$. 2HCl, MW 273.9; $^1$H-NMR (200 MHz, $d_6$-DMSO) ppm: 4.13 (s, 2H); 5.82 (s, 4H), 7.24 (d, 1H), 7.55 (dd, 1H), 7.73 (s, 1H), 8.57 (s, 2H). Since the free base is used in the cyclization step, the hydrochloride was suspended in aqueous ammonia, stirred for some minutes after that the free base precipitates. The solid is filtered and dried (yield is quantitative).

EXAMPLE 2

[6-(2-methyl-1H-imidazol-1-yl)-2-phenyl]quinazoline

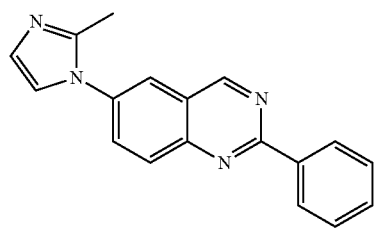 [SMILES: Cc1nccn1-c1ccc2nc(-c3ccccc3)ncc2c1]

6-bromo-2-phenyl-quinazoline (1.43 g, 5.0 mmol) and 2-methylimidazole (0.50 g, 6 mmol) were mixed with PEG 400 (d: 1.126, 1.0 g, 885 μL) and 4,7-dimethoxy-1,10-phenantroline (186 mg, 0.75 mmol), to this mixture $Cu_2O$ (38.5 mg, 0.25 mmol) and $Cs_2CO_3$ (2.29 g, 7.0 mmol) were added. The resulting reaction mixture was heated at 110° C., under argon atmosphere, for 24 hours. After cooling at r.t., the mixture was diluted with DCM (50 mL) and filtered over celite, the cake was washed with DCM and the combined filtrate and washings were evaporated to dryness. The residue was purified by chromatography ($SiO_2$, EtOAc/MeOH 95.5). The pure title compound was isolated as pale yellow solid, 1.02 g (yield: 71%), m.p.: 198.3-200.3° C. $C_{18}H_{14}N_4$, MW: 286.34; MS: m/z 287 (M+H); $^1$H-NMR (200 MHz, $d_6$-DMSO) ppm: 2.40 (s, 1H), 7.0 (s, 1H), 7.40 (s, 1H), 7.60 (m, 3H), 8.10-8.30 (m, 3H), 8.60 (m, 2H), 9.80 (s, 1H).

Alternatively 6-(2-methyl-1H-imidazol-1-yl)-2-phenyl-quinazoline can be prepared from 4-(4-methyl-1H-imidazol-1-yl)-2-aminomethylaniline:

EXAMPLE 2 (B)

6-(2-methyl-1H-imidazol-1-yl)-2-phenyl-quinazoline (alternate route)

4-(2-methyl-1H-imidazol-1-yl)-2-aminomethylaniline (2.0 g, 10 mmol) and methyl benzimidate hydrochloride (3.5 g, 20 mmol; RN: 5873-90-5, Aldrich) were dissolved in methanol (50 mL), the resulting mixture was heated at reflux for 2 hours, during this time the aminomethyl-derivative was converted into the corresponding benzamidine. After that, the methanol was evaporated and the residue taken up with glacial acetic acid (50 mL), the reaction mixture was heated at reflux for 1.5 hours. After cooling at r.t. the reaction mixture was diluted with toluene (50 mL) and evaporated. The residue was taken up with AcOEt (400 mL), washed with aq. ammonia, with water, then dried and concentrated. The obtained oily residue was dissolved in DCM (400 mL) and $MnO_2$ (6.0 g, 70 mmol) was added at r.t., in three portions, over 2 hours. The resulting suspension was stirred at r.t. for 24 hrs, then filtered over celite and the cake was rinsed with DCM. The combined filtrate and washings were concentrated and the residue chromatographed over silica gel (DCM/MeOH/$NH_3$, 85:25.2) the appropriate combined fractions were evaporated and the residue taken up with ethyl ether, heated at reflux for 5 minutes then cooled at 25° C. to crystallize the titled product as slightly brown powder (2.0 g; yield: 74%). $C_{18}H_{14}N_4$, MW: 286.34; MS: m/z 287 (M+H); $^1$H-NMR (200 MHz, $d_6$-DMSO) ppm: 2.40 (s, 1H), 7.0 (s, 1H), 7.40 (s, 1H), 7.60 (m, 3H), 8.10-8.30 (m, 3H), 8.60 (m, 2H), 9.80 (s, 1H).

EXAMPLE 3

[6-(2-methyl-1H-imidazol-1-yl)-2-(4-methoxyphenyl)]quinazoline

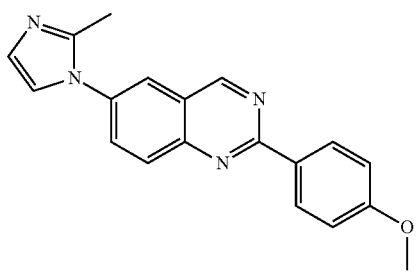 [SMILES: COc1ccc(-c2ncc3cc(-n4ccnc4C)ccc3n2)cc1]

Analogously prepared in 69% yield, starting from 4-(2-methyl-1H-imidazol-1-yl)-2-aminomethylaniline (2.0 g, 10 mmol) and methyl (4-methoxy)benzimidate hydrochloride. Slight grey powder, mp.: 198.3-200.3° C. $C_{19}H_{16}N_4O$, MW: 316.37. MS: m/z 317 (M+1). $^1$H-NMR (200 MHz, $d_6$-DMSO) ppm: 2.42 (s, 3H), 3.33 (s, 3H), 7.01 (s, 1H), 7.50 (s, 1H), 7.59-7.63 (m, 2H), 8.11-8.32 (m, 3H), 8.58-8.63 (m, 2H), 9.79 (s, 1H). FT-IR (ATR) cm$^{-1}$: 1624, 1588, 1557, 1496, 1414, 1300, 1271, 1165, 843, 761.

4-(4-methyl-1H-imidazol-1-yl)-2-aminomethylaniline dihydrochloride

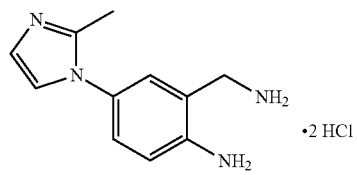

To 4-(2-methyl-1H-imidazol-1-yl)-2-cyanoaniline (7.8 g; 39 mmol) dissolved in 10% NH$_3$/methanol (70 mL) was added Raney-Nichel (2 g), the resulting mixture was hydrogenated at 60° C., at an hydrogen pressure of 60 bar, for 12 hours. The nitrogen purged reaction mixture was filtered on celite, the cake was washed with methanol and the combined filtrate and washings evaporated, the residue was dissolved in methanol, filtered and HCl was bubbled at 0° C. to provide the title product as yellow-orange solid (6.1 g, 60%). C$_{10}$H$_{12}$N$_4$.2HCl MW 263.23. MS: m/z 202 (M+1). $^1$H-NMR (300 MHz, CDCl$_3$) ppm: 2.20 (s, 3H), 3.64 (s, 2H), 5.35 (s, 2H), 6.68 (d, 1H), 6.82 (d, 1H), 6.94 (dd, 1H), 7.05-7.07 (m, 2H). The free base used in the above step was obtained by suspending the dihydrochloride in concentrated ammonia, stirring the suspension 5 min. then filtering the precipitate which was washed with water and dried.

4-(2-methyl-1H-imidazol-1-yl)-2-cyanoaniline

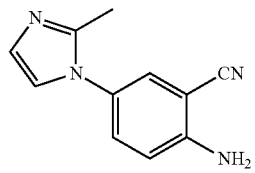

SnCl$_2$.2H$_2$O (60.0 g; 0.26 mol) was dissolved in 37% HCl (100 mL), to this solution cooled to −10° C., 4-(2-methyl-1H-imidazol-1-yl)-2-cyano-nitrobenzene (12.0 g, 50 mmol) was added in two portions over the course of 30 min. Completed the additions the stirred reaction mixture was allowed to come to r.t., and after further 45 min. stirring, it was poured in ice/water (250 g) and 3N KOH (500 mL). The resulting suspension was filtered and the cake washed with water. The residue was suspended in 2M NH$_3$/EtOH (250 mL), stirred for a few minutes and filtered, the filtrate was concentrated to provide the titled compound as a brown solid (8 g, 78%). C$_{11}$H$_{10}$N$_4$, MW: 198.23. MS: m/z 199 (M+1). $^1$H-NMR (300 MHz, CDCl$_3$) ppm: 2.21 (s, 3H), 4.70 (s, 2H), 6.79 (d, 1H), 6.97 (d, 1H), 7.22 (dd, 1H), 7.29 (d, 1H).

4-(2-methyl-1H-imidazol-1-yl)-2-cyanonitrobenzene

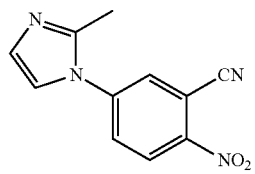 [SMILES: Cc1nccn1-c1ccc([N+](=O)[O-])c(C#N)c1]

2-cyano-4-fluoronitrobenzene (9.8 g, 59 mmol) and 2-methylimidazole (14.5 g, 177 mmol) were dissolved in dry acetonitrile (300 mL), the reaction mixture was then heated at 90° C. for 5 hours.

The solution was cooled at r.t. and the solvent evaporated, the residue was partitioned between AcOEt/0.5N HCl (5/1), the separated organic phase was washed with water, brine and then evaporated. The orange residue was crystallized from acetone/hexane to provide 12.8 g (95%) of the titled compound. When not dry acetonitrile is used some amide is obtained as side-product.

$^1$H-NMR (300 MHz, CDCl$_3$) ppm: 2.47 (s, 3H), 7.70 (d, 1H), 7.12 (d, 1H), 7.73 (dd, 1H), 7.83 (d, 1H), 8.46 (d, 1H).

EXAMPLE 4

[6-(4-methyl-1H-imidazol-1-yl)-2-phenyl]quinazoline

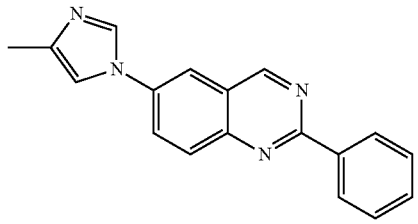 [SMILES: Cc1cn(-c2ccc3nc(-c4ccccc4)ncc3c2)cn1]

4-(4-methyl-1H-imidazol-1-yl)-2-aminomethylaniline (2.0 g, 10 mmol) and methyl benzimidate hydrochloride (1.73 g, 10 mmol; RN: 5873-90-5, Aldrich) were dissolved in methanol (15 mL), the resulting mixture was heated at reflux for 2 hours, during this time the aminomethyl-derivative was converted into the corresponding benzamidine. After that, methanol was evaporated and the residue taken up with glacial acetic acid (15 mL), the reaction mixture was heated at reflux for 2 hours. After cooling at r.t. the reaction mixture was diluted with toluene (50 mL) and evaporated. The residue was taken up with AcOEt (200 mL), washed with aq. ammonia and then with water, dried and concentrated. The oily residue was dissolved in DCM (200 mL) and MnO$_2$ (6.0 g, 70 mmol) was added at r.t., in three portions, over 2 hours. The resulting suspension was stirred at r.t. for 22 hrs, then filtered over celite, and the cake was rinsed with DCM. The combined filtrate and washings were concentrated and the residue was taken up with ethyl ether, heated at reflux for 5 minutes then cooled at 25° C., to crystallize the title product as off white powder (2.3 g; yield: 85%), melting at 201.9-202.8° C. C$_{18}$H$_{14}$N$_4$, MW: 286.34. MS: m/z 287 (M+H); $^1$H-NMR (400 MHz, d$_6$-DMSO) ppm: 2.21 (s, 3H), 7.57-7.60 (m, 3H), 7.65 (s, 1H), 8.17 (d, 1H), 8.33-8.38 (m, 3H), 8.54-8.58 (m, 2H), 9.68 (s, 1H). FT-IR (ATR) cm$^{-1}$: 1626, 1585, 1555, 1503, 1442, 1390, 1253, 1060, 838, 711.

EXAMPLE 5

[6-(5-methyl-1H-imidazol-1-yl)-2-phenyl]quinazoline

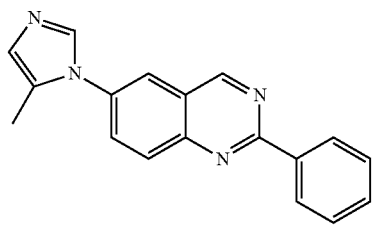 [SMILES: Cc1cncn1-c1ccc2nc(-c3ccccc3)ncc2c1]

Analogously prepared in 74% yield, starting from 4-(5-methyl-1H-imidazol-1-yl)-2-aminomethylaniline (2.0 g, 10 mmol) and methyl benzimidate hydrochloride (1.73 g, 10 mmol).

Light brown powder, mp.: 138.5-139.1° C. $C_{18}H_{14}N_4$, MW: 286.34. MS: m/z 287 (M+H); $^1$H-NMR (400 MHz, $d_6$-DMSO) ppm: 2.27 (s, 3H), 6.91 (s, 1H), 7.58-7.60 (m, 3H), 8.11 (s, 1H), 8.21 (s, 1H), 8.25 (m, 1H), 8.29 (s, 1H), 8.58 (m, 2H), 9.78 (s, 1H). FT-IR (ATR) cm$^{-1}$: 1588, 1554, 1490, 1437, 1382, 1232, 1167, 919, 812, 763, 709.

EXAMPLE 6

[6-(4-methyl-1H-imidazol-1-yl)-2-(4-methoxyphenyl)]quinazoline

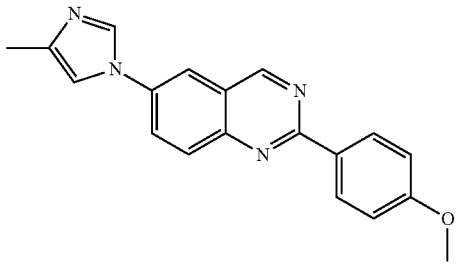

Analogously prepared in 76% yield from 4-(4-methyl-1H-imidazol-1-yl)-2-aminomethylaniline and methyl 4-methoxybenzimidate hydrochloride (RN: 39739-49-6). Colourless crystals, mp.: 201.0-202.0° C. $C_{19}H_{16}N_4O$, MW: 316.37; MS: m/z 317 (M+H); $^1$H NMR (400 MHz, $d_6$-DMSO) ppm: 2.21 (s, 3H), 3.85 (s, 3H), 7.10 (d, 2H), 7.62 (s, 1H), 8.11 (d, 1H), 8.28-8.33 (m, 3H), 8.49 (d, 2H), 9.61 (s, 1H). FT-IR (ATR) cm$^{-1}$: 1627, 1580, 1515, 1388, 1377, 1252, 1167, 1017, 836.

EXAMPLE 7

[6-(4-methyl-1H-imidazol-1-yl)-2-(2-methoxyphenyl)]quinazoline

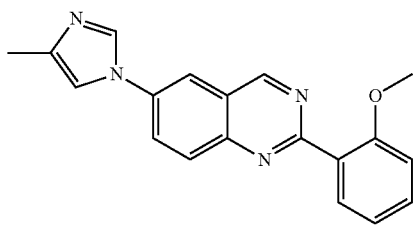

Analogously prepared from 4-(4-methyl-1H-imidazol-1-yl)-2-aminomethylaniline and methyl 2-methoxybenzimidate hydrochloride, in 65% yield. Colourless crystals, mp.: 160.6-162.0° C. $C_{19}H_{16}N_4O$, MW: 316.37; MS: m/z 317 (M+H); $^1$H NMR (400 MHz, $d_6$-DMSO) ppm: 2.21 (s, 3H), 3.79 (s, 3H), 6.98 (d, 1H), 7.08 (t, 1H), 7.11 (d, 1H), 7.50 (t, 1H), 7.63-7.67 (m, 2H), 8.14 (d, 1H), 8.27 (d, 1H), 8.33-8.40 (m, 1H), 9.64 (s, 1H). FT-IR (ATR) cm$^{-1}$: 1560, 1507, 1398, 1243, 1060, 1023, 847, 761.

EXAMPLE 8

[6-(4-methyl-1H-imidazol-1-yl)-2-(3-methoxyphenyl)]quinazoline

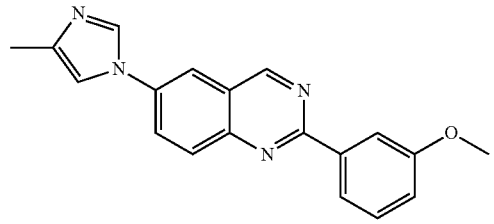

Analogously prepared from 4-(4-methyl-1H-imidazol-1-yl)-2-aminomethylaniline and methyl 3-methoxybenzimidate hydrochloride, in 68% yield. Light yellow powder, mp.: 294-296° C. $C_{19}H_{16}N_4O$, MW: 316.37; MS: m/z 317 (M+H); $^1$H NMR (400 MHz, $d_6$-DMSO) ppm: 2.22 (s, 3H), 4.09 (s, 3H), 7.16 (dd, 1H), 7.50 (t, 1H), 7.64 (s, 1H), 8.11 (s, 1H), 8.18 (t, 2H), 8.35-8.40 (m, 3H), 9.69 (s, 1H). FT-IR (ATR) cm$^{-1}$: 1627, 1556, 1487, 1451, 1384, 1269, 1211, 1036, 836, 774, 719.

EXAMPLE 9

[6-(4-methyl-1H-imidazol-1-yl)-2-(1,3-benzodioxol-5-yl)]quinazoline

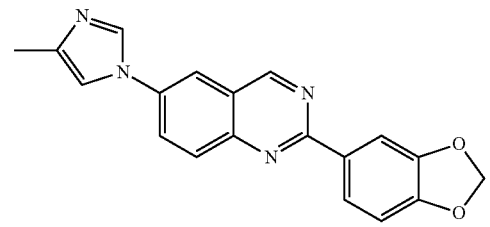 [SMILES: Cc1cn(-c2ccc3nc(-c4ccc5c(c4)OCO5)ncc3c2)cn1]

Analogously prepared in 54% yield from 4-(4-methyl-1H-imidazol-1-yl)-2-aminomethylaniline and methyl 1,3-methylendioxybenzimidate hydrochloride. Colourless crystals, mp.: 215.3-218.7° C. $C_{19}H_{14}N_4O_2$, MW: 330.35; MS: m/z 331 (M+H); $^1$H NMR (400 MHz, $d_6$-DMSO) ppm: 2.36 (s, 3H), 6.15 (s, 2H), 6.98 (d, 1H), 7.14 (s, 1H), 7.84 (s, 1H), 7.94 (m, 2H), 8.13 (s, 1H), 8.15 (d, 1H), 8.27 (d, 1H), 9.45 (s, 1H). FT-IR (ATR) cm$^{-1}$: 1557, 1503, 1444, 1380, 1248, 1036, 826.

EXAMPLE 10

[6-(4-methyl-1H-imidazol-1-yl)-2-(4-fluorophenyl)]quinazoline

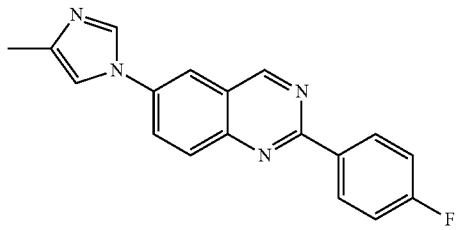 [SMILES: Cc1cn(-c2ccc3nc(-c4ccc(F)cc4)ncc3c2)cn1]

Analogously prepared in 58% yield, from 4-(4-methyl-1H-imidazol-1-yl)-2-aminomethylaniline and methyl 4-fluorobenzimidate hydrochloride, $C_{18}H_{13}N_4F$, MW: 304.33; MS: m/z 305 (M+H); $^1$H NMR (300 MHz, CDCl$_3$) ppm: 2.38 (s, 3H); 7.18-7.38 (m, 4H); 7.82-7.95 (m, 3H); 8.6-8.7 (m, 2H), 9.50 (s, 1H). FT-IR (ATR) cm$^{-1}$: 1627, 1602, 1556, 1579, 1512, 1504, 1446, 1390, 1374, 1217, 1159, 1065, 836, 825, 735, 714.

EXAMPLE 11

[6-(4-methyl-1H-imidazol-1-yl)-2-(4-methanesulfonylphenyl)]quinazoline

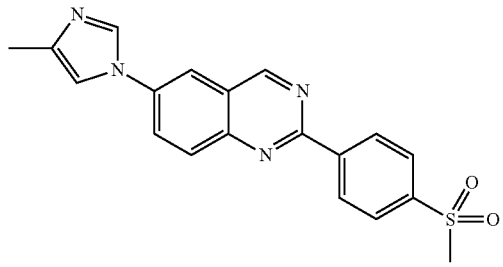 [SMILES: Cc1cn(-c2ccc3nc(-c4ccc(S(C)(=O)=O)cc4)ncc3c2)cn1]

Analogously prepared in 38% yield from 4-(4-methyl-1H-imidazol-1-yl)-2-aminomethylaniline and methyl 4-methanesulfonylbenzimidate hydrochloride, mp.: 276.4-281.7° C. $C_{19}H_{16}N_4O_2S$, MW: 364.43; MS: m/z 365 (M+H); $^1$H NMR (300 MHz, CDCl$_3$) ppm: 2.39 (s, 3H); 3.10 (s, 3H); 7.20 (s, 1H), 7.90-8.10 (m, 4H), 8.20 (dd, 4H), 8.85 (d, 2H), 9.60 (s, 1H). $^1$H NMR (400 MHz, CDCl$_3$) ppm: 2.38 (s, 3H); 3.15 (s, 3H), 7.21 (s, 1H), 7.93 (s, 1H), 7.97 (s, 1H), 7.98 (dd, 1H), 8.14 (d, 1H), 8.26 (d, 1H), 8.87 (d, 1H), 9.57 (s, 1H).

EXAMPLE 12

[6-(4-methyl-1H-imidazol-1-yl)-2-(3-furyl)]quinazoline

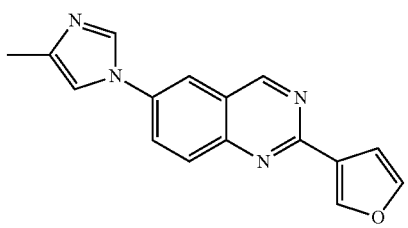 [SMILES: Cc1cn(-c2ccc3nc(-c4ccoc4)ncc3c2)cn1]

Analogously prepared from 4-(4-methyl-1H-imidazol-1-yl)-2-aminomethylaniline and 3-furanecarboximidic acid methyl ester hydrocloride, in 33% yield, mp.: 160.5-163.2° C. $C_{16}H_{12}N_4O$, MW: 276.30; MS: m/z 277 (M+H); $^1$H NMR (300 MHz, CDCl$_3$) ppm: 2.35 (s, 3H); 7.15 (d, 2H), 7.51 (s, 1H), 7.80 (s, 1H) 7.90-7.95 (m, 2H), 8.10 (d, 1H), 8.40 (s, 1H), 9.40 (s, 1H). $^1$H NMR (400 MHz, d$_6$-DMSO) ppm: 2.21 (s, 3H); 7.17 (s, 1H), 7.63 (s, 1H), 7.87 (m, 1H) 8.08 (d, 1H), 8.31 (dd, 1H), 8.35 (s, 1H), 8.56 (s, 1H), 9.57 (s, 1H). FT-IR (ATR) cm$^{-1}$: 1629, 1588, 1576, 1558, 1501, 1379, 1148, 1059, 1007, 862, 815, 723.

4-(4-methyl-1H-imidazol-1-yl)-2-aminomethylaniline

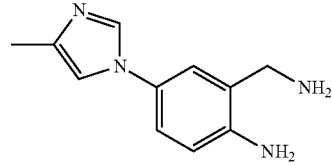

To 4-(4-methyl-1H-imidazol-1-yl)-2-cyanoaniline (15.5 g; 78.2 mmol) dissolved in 10% NH$_3$/methanol was added Raney-Nichel (5 g), the resulting mixture was hydrogenated at 60° C., at an hydrogen pressure of 60 bar, for 24 hours. The nitrogen purged reaction mixture was filtered on celite, the cake was washed with methanol and the combined filtrate and washings evaporated. The residue was purified by column chromatography over silica gel (DCM/MeOH/2M NH$_3$, 85:10:5) evaporation of the combined appropriate fractions afforded the pure titled product as yellow-orange solid (12.9 g, 82%). $C_{11}H_{14}N_4$, MW: 202.26; $^1$H-NMR (300 MHz, d$_6$-DMSO) ppm: 2.13 (s, 3H), 5.24 (s, 2H), 6.67 (d, 1H), 7.08 (dd, 1H), 7.17 (t, 1H), 7.23 (d, 1H), 7.81 (d, 1H).

4-(5-methyl-1H-imidazol-1-yl)-2-aminomethylaniline

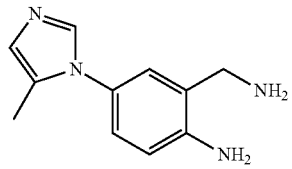

Prepared in 66% yield as above described, starting from 4-(5-methyl-1H-imidazol-1-yl)-2-cyanoaniline. $C_{11}H_{14}N_4$, MW: 202.26; $^1$H-NMR (300 MHz, d$_6$-DMSO) ppm: 2.07 (s, 3H), 5.38 (s, 2H), 6.89 (d, 1H), 6.73 (t, 1H), 6.94 (dd, 1H), 7.06 (d, 1H), 7.53 (d, 1H).

4-(4-methyl-1H-imidazol-1-yl)-2-cyanoaniline

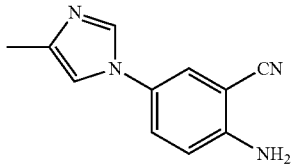

SnCl$_2$.2H$_2$O (119.0 g; 0.526 mol) was dissolved in 37% HCl (240 mL), to this solution cooled to −10° C., 4-(5-methyl-1H-imidazol-1-yl)-2-cyano-nitrobenzene (24.0 g, 105.0 mmol) was added in five portions over the course of 20 min. Completed the additions, the stirred reaction mixture was allowed to come to r.t., and after further 45 min. stirring, it was poured in ice/water (500 g) and 3N KOH (1.0 L). The resulting suspension was filtered and the cake washed with water, the residue was suspended in 2M NH₃/EtOH (250 mL), stirred for few minutes and filtered, the filtrate was concentrated to provide the titled compound as a brown solid (15.9 g, 76%). $C_{11}H_{10}N_4$, MW: 198.23; ¹H-NMR (300 MHz, CDCl₃) ppm: 2.2 (s, 3H), 6.79 (d, 1H), 6.81 (d, 1H), 6.84 (t, 1H), 7.75 (dd, 1H), 7.28 (d, 1H), 7.30-7.34 (m, 1H), 7.57 (d, 1H).

4-(5-methyl-1H-imidazol-1-yl)-2-cyanoaniline

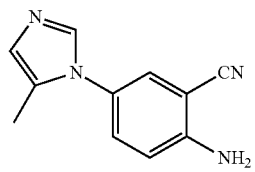

Prepared in 64% yield as above described, starting from 4-(5-methyl-1H-imidazol-1-yl)-2-cyanonitrobenzene. $C_{11}H_{10}N_4$, MW: 198.23; ¹H-NMR (300 MHz, CDCl₃) ppm: 2.09 (s, 3H), 6.81-6.84 (m, 2H), 7.20 (dd, 1H), 7.26 (d, 1H), 7.44 (d, 1H).

4-(4-methyl-1H-imidazol-1-yl)-2-cyanonitrobenzene

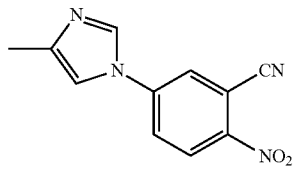 [SMILES: Cc1cn(-c2ccc([N+](=O)[O-])c(C#N)c2)cn1]

2-cyano-4-fluoronitrobenzene (29.5 g, 177.6 mmol) and 4-methylimidazole (29.1 g, 354.4 mmol) were dissolved in acetonitrile (300 mL), the reaction mixture was then heated at 90° C. for 3 hours.

The solution was cooled at r.t. and the solvent evaporated, the residue (constituted of about 85:15 regioisomeric mixture of 4/5 methyl-isomers) was partitioned between AcOEt/H₂O (5/2), the separated organic layer was washed with water, brine and then evaporated. The orange residue was crystal-lized from acetone/heptane. This gave a first crop of the titled product 25.0 g (62%), the mother liquor was concentrated and the residue was chromatographed over silica gel (acetone/heptane 1:3 to 1:1, to 3:1) to provide further 7.0 g (17.2%) of the pure title compound.

TLC: (SiO₂, 245 nm) acetone/heptane (3:1) Rf: 0.50; $C_{11}H_{10}N_4O_2$, MW: 230.23; ¹H-NMR (300 MHz, CDCl₃) ppm: 2.3 (s, 3H), 7.10 (t, 1H), 7.63 (d, 1H), 7.75 (dd, 1H), 7.86 (d, 1H), 7.91 (d, 1H), 8.44 (d, 1H).

4-(5-methyl-1H-imidazol-1-yl)-2-cyanonitrobenzene

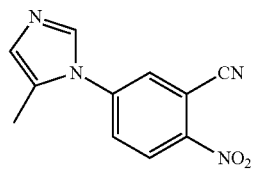 [SMILES: Cc1cncn1-c1ccc([N+](=O)[O-])c(C#N)c1]

Obtained from the column chromatography above described as yellow-orange solid (7.2 g; 17.8%).

TLC: (SiO₂, 245 nm) acetone/heptane (3:1) Rf: 0.30; $C_{11}H_{10}N_4O_2$, MW: 230.23; ¹H-NMR (300 MHz, CDCl₃) ppm: 2.3 (s, 3H), 7.0 (t, 1H), 7.63 (d, 1H), 7.74 (dd, 1H), 7.84 (d, 1H), 8.49 (d, 1H).

General Procedure for the Preparation of Iminoester Hydrochlorides

Iminoester hydrochlorides used as reagents in this invention can be prepared according to procedures well known in literature, for example: J. Org. Chem. 69(20), 6572-6589; 2004, J. Med. Chem., 38(8), 1287-94; 1995, below two representative procedures are herein reported as examples.

Methyl 4-methoxybenzimidate hydrochloride

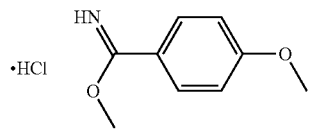

4-methoxybenzonitrile (12.5 g, 91.1 mmol) was dissolved in methanol (140 mL), through this cooled (−5° C.) solution gaseous HCl was bubbled for about 3 hours. The reaction mixture was then stirred, in a closed flask, at r.t. for 24 hours. Then the excess HCl was stripped by bubbling nitrogen and the resulting solution was concentrated, the residue was taken up with TBME (100 mL) and stirred for 30 min., then filtrated and dried to provide the title product as a colourless powder 19.0 g (quantitative). $C_9H_{11}NO_2 \cdot HCl$, MW: 201.69 ¹H-NMR (300 MHz, D₂O) ppm: 4.20 (s, 3H), 6.9 (m, 1H); 7.65 (m, 1H); 8.40 (m, 1H).

3-Furanecarboximidic Acid Methyl Ester Hydrocloride

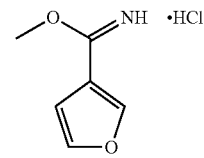

3-Furonitrile (1.0 g; 10.8 mmol) was dissolved in dry MeOH (12 mL), the solution was cooled at −5° C. and gaseous HCl was bubbled for 30 min., then the reaction vessel was closed, the temperature allowed to come to r.t. and the reaction mixture stirred overnight. The excess HCl was removed by bubbling nitrogen, then the solvent was evaporated and the residue suspended in TBME (30 mL), filtered and dried to provide the title product, 1.09 g (63%). $C_6H_7NO_2 \cdot HCl$, MW: 161.59; ¹H-NMR (300 MHz, D₂O) ppm: 3.80 (s, 3H), 4.20 (s, 3H), 7.0 (d, 2H); 7.90 (d, 2H).

EXAMPLE 13

[6-(1H-imidazol-1-yl)-2-(1,3-benzodioxol-5-yl)]quinazoline

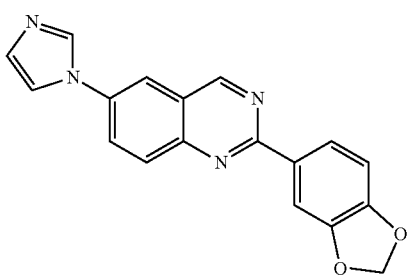 [SMILES: c1cn(-c2ccc3nc(-c4ccc5c(c4)OCO5)ncc3c2)cn1]

A suspension of 6-amino-2-(1,3-benzodioxol-5-yl)-quinazoline (2.5 g, 9.4 mmol) (WO2008/014822) and 40% aqueous glyoxal (1.1 ml, 9.4 mmol) in methanol (20 ml) was stirred at r.t. for 18 h. NH$_4$Cl (1.0 g, 0.019 mol), 37% aqueous formaldehyde (1.4 ml, 19 mmol) and methanol (200 ml) were added and the mixture was refluxed for 1 h. 85% H$_3$PO$_4$ (1.4 ml) was added and the mixture was heated at reflux for a further 4 h. The solvent was removed and the residue was poured in water, and basified with aq. NaOH. The precipitate was filtered, washed with water and dissolved in DCM. The product was extracted with diluted aqueous HCl. To the collected aqueous layers Na$_2$CO$_3$ was added and the resulting mixture extracted with chloroform, which was washed with water and dried, concentrated and the resulting solid was suspended in isopropyl ether. The solid was filtered and dried to afford the title product (2.0 g, 29% yield). C$_{18}$H$_{12}$N$_4$O$_2$, MW: 316.32. mp 217-218° C. $^1$H NMR (200 MHz, d$_6$-DMSO) ppm: 6.16 (s, 2H); 7.12 (d, 1H), 7.21 (s, 1H), 8.00 (d, 2H), 8.14-8.22 (m, 2H), 8.36-8.50 (m, 3H), 9.65 (s, 1H). FT-IR (KBr) 1504, 1446, 1251.

EXAMPLE 14

[6-(1H-imidazol-1-yl)-2-(benzofuran-5-yl)-]quinazoline dihydrochloride trihydrate

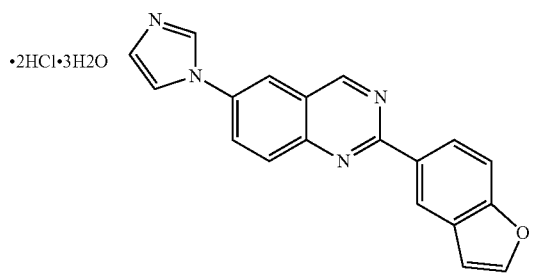 [SMILES: c1cn(-c2ccc3nc(-c4ccc5occc5c4)ncc3c2)cn1]

Was analogously prepared in 20% yield starting from 6-amino-2-(benzofurane-5-yl)-quinazoline (WO2008/014822). C$_{19}$H$_{12}$N$_4$O. 2HCl. 3H$_2$O; MW: 439.30; mp 284.7-285.1° C.; $^1$H NMR (200 MHz, d$_6$-DMSO) ppm: 7.15 (s, 1H); 7.78 (d, 1H), 8.02 (s, 1H), 8.10 (d, 1H), 8.29 (d, 1H), 8.47 (m, 2H), 8.58 (d, 1H), 8.71 (d, 1H), 8.90 (s, 1H), 9.78 (s, 1H), 10.00 (s, 1H). FT-IR (KBr): 3399, 3097, 1614.

EXAMPLE 15

[6-(1H-imidazol-1-yl)-2-(2,3-dihydro-1,4-benzodioxin-6-yl)]quinazoline

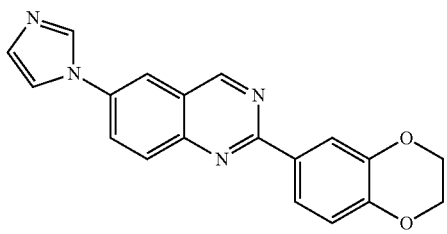 [SMILES: c1cn(-c2ccc3nc(-c4ccc5c(c4)OCCO5)ncc3c2)cn1]

Was analogously prepared in 25% yield starting from 6-amino-2-(2,3-dihydro-1,4-benzodioxin-6-yl)-quinazoline (WO2008/014822), C$_{19}$H$_{14}$N$_4$O$_2$, MW: 330.35; mp 131.5-131.9° C.; $^1$H NMR (200 MHz, d$_6$-DMSO) ppm: 4.34 (s, 4H), 7.04 (d, 1H), 7.21 (s, 1H), 7.97 (d, 1H), 8.03-8.13 (m, 2H), 8.18 (s, 1H), 8.32-8.43 (m, 2H), 8.49 (s, 1H), 9.64 (s, 1H). FT-IR (KBr) 1555, 1507, 1286.

EXAMPLE 16

[6-(1H-imidazol-1-yl)-2-(1,3-benzodioxol-5-yl)]quinoline dihydrochloride

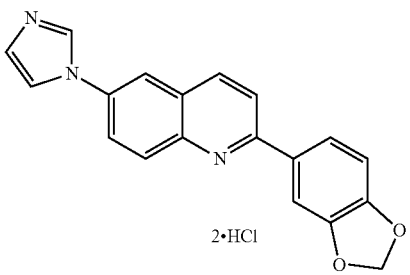 [SMILES: c1cn(-c2ccc3nc(-c4ccc5c(c4)OCO5)ccc3c2)cn1]

6-(1H-imidazol-1-yl)-2-(trifluoromethane sulfonoxy) quinoline (3.0 g; 8.6 mmol), K$_2$CO$_3$ (1.73 g; 10.4 mmol), 3,4-methylendioxyphenylboronic acid and tetrakis-triphenylphosphine palladium (0.8 g; 0.8 mmol) were mixed under stirring, in dry toluene (100 mL), under argon atmosphere, at r.t. The resulting reaction mixture was heated at reflux for 15 hours, then it was cooled at r.t. and poured in water (250 mL). The resulting precipitate was filtered, washed with water, dried and dissolved in DCM/MeOH (9:1, 10 mL,), gaseous HCl was doubled through the solution until formation of a precipitate, which was filtered and dried. The title product was obtained as di-hydrochloride (2.57 g; 88% yield) melting at: 314.0-315° C. C$_{19}$H$_{13}$N$_3$O$_2$.2HCl, MW: 351.79. $^1$H-NMR (200 MHz, d$_6$-DMSO) ppm: 6.05 (s, 2H), 7.07 (d, 1H), 7.70-7.72 (m, 3H), 8.01-8.29 (m, 5H), 8.51 (d, 1H), 9.46 (s, 1H). FT-IR (ATR) cm$^{-1}$: 1602, 1495, 1443, 1265, 1254, 1110, 1029, 812.

EXAMPLE 17

[6-(1H-imidazol-1-yl)]-2-(phenyl)]quinoline

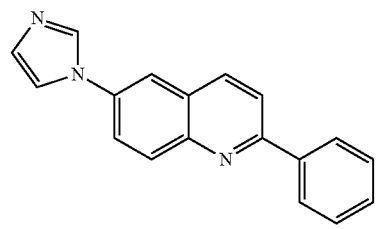 [SMILES: c1ccc(-c2ccc3cc(-n4ccnc4)ccc3n2)cc1]

Analogously prepared as colorless solid (2.7 g; yield: 89%) using phenylboronic acid in the Suzuky coupling. Crystallized from DCM/methanol as dihydrochloride, the free base was obtained by suspending the dihydrochloride in conc. aq. ammonia, and the precipitate was filtered, washed with water and dried. Colorless solid (2.3 g) melting at: 130.6-131.4° C. C$_{18}$H$_{13}$N$_3$, MW 271.32. $^1$H-NMR (200 MHz, d$_6$-DMSO) ppm: 7.20 (m, 1H), 7.75-7.63 (m, 3H), 7.94 (m, 1H), 8.11-

8.32 (m, 5H), 8.46-8.50 (m, 2H). FT-IR (ATR) cm$^{-1}$: 1625, 1598, 1500, 1325, 1244, 1054, 826, 758, 655.

EXAMPLE 18

[6-(1H-imidazol-1-yl)-2-(4-methoxyphenyl)]quinoline dihydrochloride

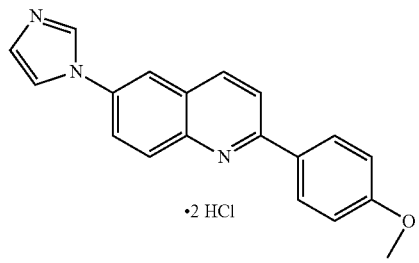 [SMILES: COc1ccc(-c2ccc3cc(-n4ccnc4)ccc3n2)cc1]

Analogously prepared in 57% yield using 4-methoxyphenylboronic acid in the Suzuky coupling, colorless solid, crystallized from DCM/methanol, mp.: 266.0-267.0° C. $C_{19}H_{15}N_3O.2HCl$; MW: 374.27. $^1$H-NMR (200 MHz, d$_6$-DMSO) ppm: 3.84 (s, 3H), 7.14 (d, 2H), 7.87 (s, 1H), 8.11-8.27 (m, 6H), 8.41 (s, 1H), 8.58 (d, 1H), 9.70 (s, 1H). FT-IR (ATR) cm$^{-1}$: 1597, 1510, 1272, 1184, 1014, 825, 804.

EXAMPLE 19

[6-(1H-imidazol-1-yl)-2-(2-methoxyphenyl)]quinoline dihydrochloride

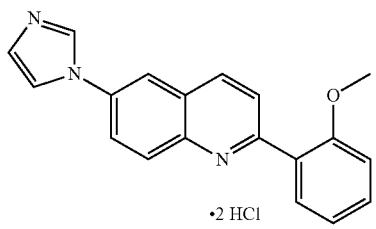 [SMILES: COc1ccccc1-c1ccc2cc(-n3ccnc3)ccc2n1]

Analogously prepared in 48% yield, using 2-methoxyphenylboronic acid in the Suzuky coupling, colorless solid, crystallized from DCM/MeOH, mp.: 251.5-252.0° C. $C_{19}H_{15}N_3O.2HCl$, MW: 374.27. $^1$H-NMR (200 MHz, D$_2$O) ppm: 3.87 (s, 3H), 7.10-7.18 (m, 2H), 7.40-7.68 (m, 4H), 7.70-7.90 (m, 5H), 8.94 (s, 1H). FT-IR (ATR) cm$^{-1}$: 1607, 1577, 1497, 1317, 1252, 1016, 828, 764, 745.

EXAMPLE 20

[6-(1H-imidazol-1-yl)-2-(3-furyl)]quinoline dihydrochloride

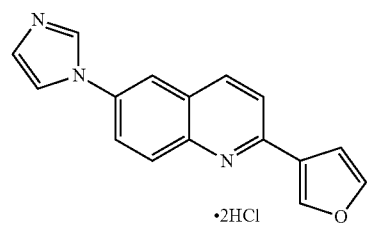 [SMILES: c1cn(-c2ccc3nc(-c4ccoc4)ccc3c2)cn1]

Analogously prepared in 81.5% yield, using 3-furylboronic acid in the Suzuky coupling. Crystallized from DCM/MeO as colorless solid, mp.: 293.1-295.6° C. $C_{16}H_{11}N_3O.2HCl$, MW: 334.20. $^1$H-NMR (200 MHz, d$_6$-DMSO) ppm: 7.30 (s, 1H), 7.86-7.90 (m, 2H), 8.1 (d, 1H), 8.15 (dd, 1H), 8.32 (d, 2H), 8.45 (d, 1H), 8.58 (d, 1H), 8.68 (s, 1H), 9.76 (s, 1H). FT-IR (ATR) cm$^{-1}$: 1651, 1624, 1547, 1328, 1159, 822.

EXAMPLE 21

[6-(1H-imidazol-1-yl)-2-(4-fluorophenyl)]quinoline dihydrochloride

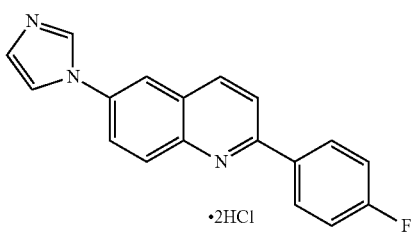 [SMILES: Fc1ccc(-c2ccc3cc(-n4ccnc4)ccc3n2)cc1]

Analogously prepared in 64.5% yield, using 4-fluorophenylboronic acid in the Suzuky coupling. Crystallized from DCM/MeOH, colorless solid, mp.: 280.7-282.0° C. $C_{18}H_{12}FN_3.2HCl$, MW: 362.31. $^1$H-NMR (200 MHz, d$_6$-DMSO) ppm: 7.42 (t, 2H), 8.03 (s, 1H), 8.22-8.61 (m, 8H), 9.94 (s, 1H). FT-IR (ATR) cm$^{-1}$: 1644, 1599, 1509, 1327, 1248, 1161, 833.

EXAMPLE 22

[6-(1H-imidazol-1-yl)-2-(4-dimethylaminophenyl)]quinoline trihydrochloride

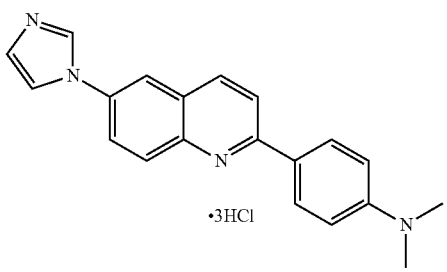 [SMILES: CN(C)c1ccc(-c2ccc3cc(-n4ccnc4)ccc3n2)cc1]

Analogously prepared as colorless solid (yield: 84.5%) using 4-dimethylaminophenylboronic acid in the Suzuky coupling. Crystallized from DCM/MeOH pale red solid, mp.: 284-286° C. $C_{20}H_{18}N_4.3HCl$, MW: 423.77. $^1$H-NMR (200 MHz, d$_6$-DMSO) ppm: 3.0 (s, 6H), 6.98 (d, 2H), 7.83 (s, 1H), 8.14 (d, 2H), 8.23-8.39 (m, 4H), 8.74 (d, 2H), 9.65 (s, 1H). FT-IR (ATR) cm$^{-1}$: 1640, 1591, 1546, 1387, 1339, 1202, 1133, 812.

EXAMPLE 23

[6-(1H-imidazol-1-yl)-2-(4-trifluoromethoxyphenyl)]quinoline dihydrochloride

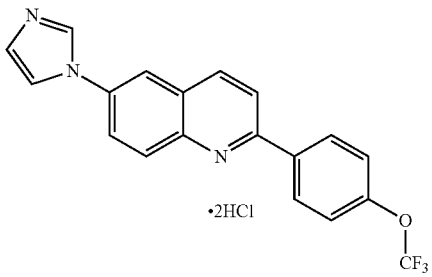 [SMILES: FC(F)(F)Oc1ccc(-c2ccc3cc(-n4ccnc4)ccc3n2)cc1]

Analogously prepared as colorless solid (1.62 g; yield: 78%) using 4-trifluoromethox-phenylboronic acid in the Suzuky coupling. Crystallized from DCM/methanol, colorless solid, mp.: 260-262° C. $C_{19}H_{12}F_3N_3O.2HCl$, MW: 428.24. $^1$H-NMR (200 MHz, $d_6$-DMSO) ppm: 7.59 (d, 2H), 8.03 (s, 1H), 8.23-8.63 (m, 7H), 9.92 (s, 1H). FT-IR (ATR) cm$^{-1}$: 1619, 1326, 1251, 1184, 1149, 849, 830.

EXAMPLE 24

[6-(1H-imidazol-1-yl)-2-(2-methyl-4-trifluoromethoxyphenyl)]quinoline dihydrochloride

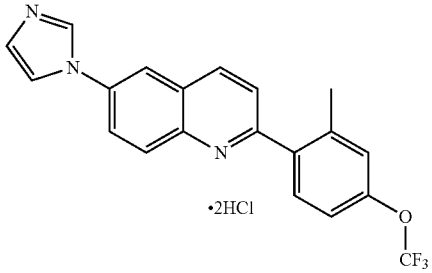 [SMILES: Cc1cc(OC(F)(F)F)ccc1-c1ccc2cc(-n3ccnc3)ccc2n1]

Analogously prepared in 78% yield, using (2-methyl-4-trifluoromethoxyphenyl)boronic acid in the Suzuky coupling. Crystallized from DCM/MeOH, slight grey powder melting at 269.7-274.5° C.
$C_{20}H_{14}F_3N_3O.2HCl$, MW: 442.27. $^1$H-NMR (200 MHz, $d_6$-DMSO) ppm: 2.83 (s, 3H), 7.40 (d, 1H), 7.77 (s, 1H), 8.80-8.57 (m, 8H), 9.60 (s, 1H). FT-IR, (ATR) cm$^{-1}$: 1638, 1616, 1270, 1224, 1149, 900, 885.

EXAMPLE 25

[6-(1H-imidazol-1-yl)-2-(4-methanesulfonylphenyl)]quinoline dihydrochloride

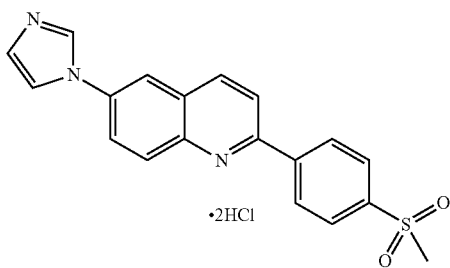 [SMILES: CS(=O)(=O)c1ccc(-c2ccc3cc(-n4ccnc4)ccc3n2)cc1]

6-(1H-imidazol-1-yl)-2-(trifluoromethane sulfonoxy)quinoline (1.06 g; 2.88 mmol) was dissolved in dry dioxane (35 mL), then LiCl (1.0 g, 2.88 mmol) and hexamethylditin (1 g, 2.88 mmol) and tretrakis-triphenylphosiphine palladium (25 mg, 0.02 mmol) were added under argon atmosphere. To the stirred suspension, 4-bromo-methanesulfonylbenzene (0.7 g, 3.0 mmol) dissolved in dry dioxane (3 mL) was added at r.t. The resulting mixture was then refluxed for 48 hours, then cooled at r.t. and poured into water (100 mL). The resulting suspension was saturated with NaHCO$_3$ and the precipitate was extracted with AcOEt. The organic layer was washed with water then dried and concentrated to afford a brown solid. The product was dissolved in DCM/MeOH (9:1) and the hydrochloride was precipitated by bubbling gaseous HCl. After crystallization from water the title product (600 mg, yield: 48%) was obtained as light-yellow solid melting at: 267.4-268.1° C. $C_{19}H_{15}N_3O_2S.2HCl$, MW: 422.33. $^1$H-NMR (200 MHz, $d_6$-DMSO) ppm: 3.32 (s, 3H) 7.83 (s, 1H), 8.14 (d, 2H), 8.23-8.66 (m, 7H), 9.58 (s, 1H). FT-IR (ATR), cm$^{-1}$: 1600, 1508, 1298, 1140, 1090, 963, 820, 774.

6-(1H-imidazol-1-yl)-2-(trifluoromethane sulfonoxy)quinoline

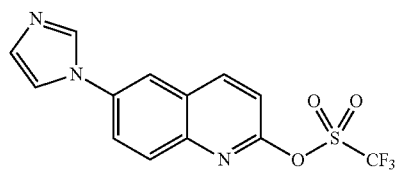 [SMILES: O=S(=O)(Oc1ccc2cc(-n3ccnc3)ccc2n1)C(F)(F)F]

Sodium hydride (60% suspension in mineral oil, 8.7 g; 219.6 mmol) was added portion-wise, under stirring at −3° C., under argon atmosphere, to a solution of 6-(1H-imidazol-1yl)-2-quinolinone hydrochloride (22 g; 87.8 mmol) in dry DMF (250 mL). Completed the additions the reaction mixture was cooled at −15° C., and Bis(trifluoromethylsulfonyl)phenylamine (37.25 g, 104.25 mmol; RN: 37595-74-7, Aldrich) dissolved in dry DMF (100 mL) was added drop-wise, at such a rate to maintain the reaction temperature below −10° C. At the end of the addition the reaction temperature was allowed to rise to r.t., and the reaction mixture is stirred for further 2 hours. The reaction was then quenched in water (2.2 L), the precipitate was filtered, washed with water and then with hexane. The product was dissolved in DCM/methanol (9:1; 800 mL) and dried with Na$_2$SO$_4$. Concentration of the solution gave rise to crystallization of the titled product as a white solid which was filtered and dried (23.6 g; 77.8%). $C_{13}H_8F_3N_3O_3S$, MW: 343.3; MS (ESI) m/z: 344 (M+1).
$^1$H-NMR (200 MHz, $d_6$-DMSO) ppm: 7.21 (s, 1H), 7.76 (d, 1H), 7.96 (s, 1H), 8.17 (d, 1H), 8.32 (dd, 1H), 8.49 (s, 2H), 8.76 (d, 1H).

6-(1H-imidazol-1-yl)-2-hydroxy-quinoline hydrochloride

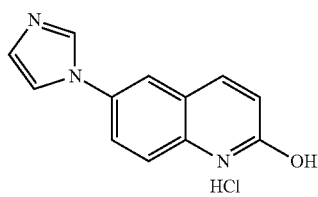 [SMILES: Oc1ccc2cc(-n3ccnc3)ccc2n1 ; Cl]

2-methoxy-6-(1H-imidazol-1-yl)-2-quinoline (26.4 g; 115.75 mmol) was suspended in 3N aqueous HCl (170 mL), the resulting reaction mixture was refluxed for 15 hours. The solution was then cooled to 0° C., the precipitated hydrochloride of the titled product was filtered and washed with isopropanol, then dried to provide 22.0 g (75.8%) of the product as colourless crystals, m.p.: 348.7-352.5° C. $C_{12}H_9N_3O \cdot HCl$, MW: 247.73. $^1$H-NMR (200 MHz, $D_2O$) ppm: 6.40 (d, 1H), 7.30 (d, 1H), 7.40 (dd, 2H), 7.48 (dd, 1H), 7.65 (d, 1H), 7.74 (d, 1H), 9.60 (s, 1H).

6-(1H-imidazol-1-yl)-2-methoxy-quinoline

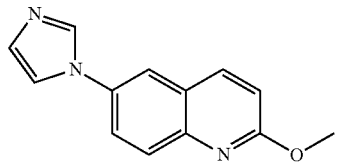 [SMILES: COc1ccc2cc(-n3ccnc3)ccc2n1]

6-bromo-2-methoxy-quinoline (19 g; 79.8 mmol; RN: 99455-05-7) was dissolved in dry DMF (100 mL), imidazole (5.7 g; 84 mmol), $K_2CO_3$ (11.6 g, 84 mmol), and CuI (1.1 g, 4.2 mmol) were added at r.t. under stirring and in argon atmosphere. The resulting mixture was heated at 150° C. for 48 hours. The reaction mixture was cooled at r.t. and poured into 2% (w/w) aqueous EDTA solution (600 mL), the resulting precipitate was filtered and washed with water, dried and then suspended in hexane/AcOEt. The resulting suspension was stirred for 10 min., filtered and the collected title product was dried, 14 g (yield 78%) of white crystals were obtained. $C_{13}H_{11}N_3O$, MW: 225.25. MS (ESI) m/z: 226 (M+1). $^1$H-NMR (200 MHz, $CDCl_3$) ppm: 3.6 (s, 3H), 6.97 (s, 1H), 7.51 (s, 1H), 7.82 (d, 1H), 8.10 (dd, 1H), 8.13 (d, 1H), 8.27 (s, 1H), 8.84 (d, 1H).

6-bromo-2-methoxy-quinoline

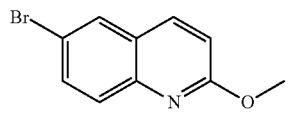

2-Chloro-6-bromo-quinoline (142.5 g, 0.6 mol; European Journal of Medicinal Chemistry, 35(10), 931-940; 2000; colourless crystals m.p.: 99.8-101.4° C.) was dissolved in methanol (700 mL), then sodium methoxide (43.9 g; 0.8 mmol) was added and the resulting reaction mixture was refluxed for 16 hours. The reaction mixture was cooled at r.t. and poured in ice-water (1.8 L), the titled product precipitated as a cream solid (133 g, 95%), melting at 157.9-161.1° C. $C_{10}H_8BrNO_2$, MW: 238.09. MS (ESI) m/z: 239 (M+1). $^1$H-NMR (200 MHz, $CDCl_3$) ppm: 4.06 (s, 3H), 6.91 (d, 1H), 7.64-7.75 (m, 2H), 7.88 (d, 2H).

EXAMPLE 26

[6-(2-methyl-1H-imidazol-1-yl)-2-(4-methoxyphenyl)]quinoline dihydrochloride

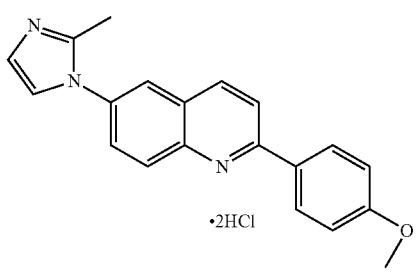 [SMILES: COc1ccc(-c2ccc3cc(-n4ccnc4C)ccc3n2)cc1]

6-(1H-2-methylimidazol-1-yl)-2-(trifluoromethane sulfonoxy)quinoline (3.77 g; 10.6 mmol) was dissolved in toluene (100 mL), then $K_2CO_3$ (4.40 g, 31.8 mmol), tetrakis-triphenylphosiphine palladium (0.733 g, 0.6 mmol), and 4-methoxyphenylboronic acid (1.74 g; 11.5 mmol) were added, at r.t., under stirring and in argon atmosphere. The resulting reaction mixture was heated at reflux for 2 hrs., then cooled at r.t. and poured in water. The organic layer was separated, the aqueous phase was extracted with DCM and the combined organic layers were dried filtered and concentrated. The resulting solid was suspended in isopropylether, stirred for 5 min. then filtered and dried. The solid was then dissolved in DCM/methanol (9:1, 30 mL) and gaseous HCl was bubbled until hydrochloride precipitation was complete. The hydrochloride was recrystallized from isopropanol/water to afford the titled product as colorless solid (720 mg; yield: 22%). $C_{20}H_{17}N_3O \cdot 2HCl$, MW: 388.38. m.p.: 230° C. (dec). MS (ESI) m/z: 316 (M+1). $^1$H-NMR (200 MHz, $d_6$-DMSO) ppm: 2.65 (s, 3H), 3.80 (s, 3H), 7.15 (d, 2H), 7.90-8.10 (m, 2H), 8.02-8.05 (m, 2H), 8.20-8.40 (m, 4H), 8.60 (d, 1H). FT-IR (ATR) $cm^{-1}$: 1598, 1510, 1269, 1170, 1013, 835.

EXAMPLE 27

[6-(2-methyl-1H-imidazol-1-yl)-2-(2-methoxyphenyl)]quinoline dihydrochloride

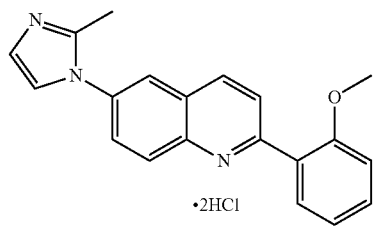 [SMILES: COc1ccccc1-c1ccc2cc(-n3ccnc3C)ccc2n1]

Analogously prepared in 35% yield, using 2-methoxyphenylboronic acid in the Suzuky coupling. Crystallized from DCM/methanol. $C_{20}H_{17}N_3O \cdot 2HCl$, MW: 388.38. m.p.: 235° C. (dec). $^1$H-NMR (400 MHz, $d_6$-DMSO) ppm: 2.65 (s, 3H), 3.88 (s, 3H), 7.17 (t, 1H), 7.26 (d, 1H), 7.54 (d, 1H), 7.83-7.86 (m, 2H), 8.02-8.05 (m, 2H), 8.15 (d, 1H), 8.37 (d, 1H), 8.41 (s, 1H), 8.61 (d, 1H). FT-IR (ATR) $cm^{-1}$: 1641, 1599, 1491, 1429, 1256, 1171, 1013, 914, 761

EXAMPLE 28

[6-(2-methyl-1H imidazol-1-yl)-2-(3-furyl)]quinoline dihydrochloride

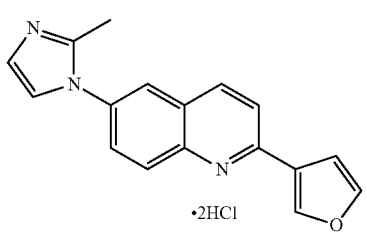 [SMILES: Cc1nccn1-c1ccc2nc(-c3ccoc3)ccc2c1]

Analogously prepared in 69% yield, using 3-furylboronic acid in the Suzuky coupling. Crystallized from toluene, mp: 240.1-243.2° C. C$_{17}$H$_{13}$N$_3$O.2HCl, MW: 348.31. $^1$H-NMR (400 MHz, d$_6$-DMSO) ppm: 2.64 (s, 3H), 7.17 (t, 1H), 7.31 (s, 1H), 7.85 (d, 1H), 7.90 (m, 1H), 8.0 (dd, 1H), 8.03 (d, 1H), 8.12 (d, 1H), 8.28-8.32 (m, 2H), 8.57 (d, 1H), 8.73 (s, 1H). FT-IR (ATR) cm$^{-1}$: 1647, 1620, 1595, 1499, 1368, 1280, 1170, 1152, 917, 860, 766.

EXAMPLE 29

[6-(2-methyl-1H imidazol-1-yl)-2-(phenyl)]quinoline dihydrochloride

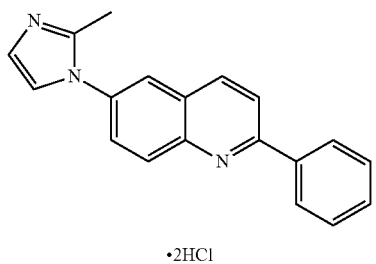 [SMILES: Cc1nccn1-c1ccc2nc(-c3ccccc3)ccc2c1]

·2HCl

Analogously prepared in 79.5% yield, using phenylboronic acid in the Suzuky coupling. Crystallized from DCM/methanol, colorless solid mp.: 296-297° C. C$_{19}$H$_{15}$N$_3$.2HCl, MW: 358.35 $^1$H-NMR (400 MHz, d$_6$-DMSO) ppm: 2.64 (s, 3H), 7.60 (m, 3H), 7.86 (d, 1H), 8.01 (dd, 1H), 8.03 (d, 1H), 8.33-8.38 (m, 5H), 8.63 (d, 1H). FT-IR (ATR) cm$^{-1}$: 1642, 1615, 1591, 1522, 1504, 1433, 1323, 1273, 1168, 921, 774, 756.

6-(1H-2-methylimidazol-1-yl)-2-(trifluoromethane sulfonoxy)quinoline

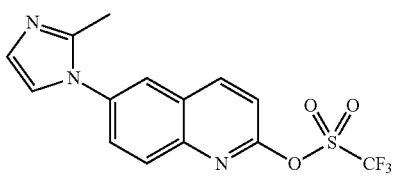 [SMILES: Cc1nccn1-c1ccc2nc(OS(=O)(=O)C(F)(F)F)ccc2c1]

6-(2-methyl-1H-imidazol-1yl)-2-quinolinone (5.14 g; 17.3 mmol) was dissolved in DMF (40 mL), then NaH (1.70 g, 60% dispersion in mineral oil, 43 mmol) was added portion-wise, under argon flow, at −10° C. The resulting mixture was stirred at 0° C. for 15 min. then cooled at −15° C., and bis(trifluoromethylsulfonyl)phenylamine (7.22 g, 20.2 mmol), dissolved in dry DMF (25 mL) is added drop-wise. The resulting mixture was stirred at −15° C. for 30 min. then allowed to come to r.t. and stirred at that temperature for 1.5 hours. The reaction mixture is then poured in water (150 mL) the resulting precipitate is filtered and dried by co-evaporation with toluene. The product is than stirred with hexane few minutes, filtered and dried to provide the title product (5.3 g; yield: 88%). C$_{14}$H$_{10}$F$_3$N$_3$O$_3$S, MW: 357.3; MS (ESI) m/z: 358 (M+1). $^1$H-NMR (400 MHz, d$_6$-DMSO) ppm: 2.4 (s, 3H), 7.0 (s, 1H), 7.52 (s, 1H), 7.79 (d, 1H), 8.0 (dd, 1H), 8.15 (d, 1H), 8.31 (s, 1H), 8.82 (d, 1H). FT-IR (ATR) cm$^{-1}$: 1666, 1511, 1414, 1207, 1130, 912, 862.

6-(2-methyl-1H-imidazol-1-yl)-2-hydroxy-quinoline hydrochloride

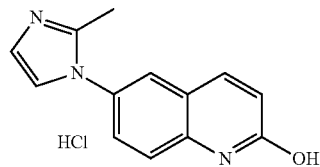 [SMILES: Cc1nccn1-c1ccc2nc(O)ccc2c1 ; Cl]

3-ethoxy-N-[4-(2-methyl-1H-imidazol-1-yl)phenyl]acrylamide (30 g; 110 mmol) was added at −5/−10° C. to concentrated sulfuric acid (120 mL) and the resulting mixture was stirred at r.t. overnight. The reaction mixture was quenched in ice/water (400 g), the pH was adjusted to pH=8 by adding K$_2$CO$_3$, the precipitate was filtered and then suspended in AcOEt/MeOH (9:1; 400 mL). The resulting suspension was stirred for 5 min., the inorganic salts were filtered off, washed with AcOEt and the combined filtrate and washings, dried and concentrated. Column chromatography of the residue over silica gel (AcOEt/MeOH 9:1) afforded 15.3 g (62%) of an amorphous grey solid. This solid was dissolved at 60° C. in 3 N HCl (150 mL), on cooling the hydrochloride crystallized, as a pale yellow solid which was filtered, washed with iso-propanol and dried to afford the pure title product 13.8 g, (48%). C$_{13}$H$_{11}$N$_3$O.HCl, MW: 261.75; $^1$H-NMR (200 MHz, D$_2$O) ppm: 2.44 (s, 3H), 6.40 (d, 1H), 7.30 (d, 1H), 7.40 (dd, 2H), 7.48 (dd, 1H), 7.65 (d, 1H), 7.74 (d, 1H).

3-ethoxy-N-[4-(2-methyl-1H-imidazol-1-yl)phenyl] acrylamide

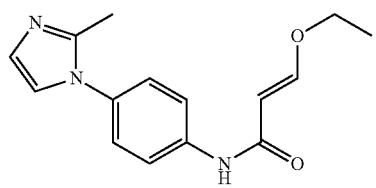 [SMILES: CCO/C=C/C(=O)Nc1ccc(-n2ccnc2C)cc1]

4-(2-methyl-1H-imidazol-1-yl)aniline (40.7 g, 232 mmol; RN: 74852-81-6, Maybridge, J. Med. Chem., 48(6), 1729-1744; 2005) was dissolved in dry pyridine (290 mL), 3-ethoxyacryloyl chloride (36.1 g, 268 mmol) was then added dropwise at 0°/−10° C. The resulting mixture was stirred at 0° C. for 2 hours and at r.t. overnight. The reaction mixture was quenched with 100 mL of water, and pyridine was distilled i.v., the residue was taken up with water and the pH was adjusted to pH=10, by adding K$_2$CO$_3$, the resulting suspension was extracted with AcOEt and concentrated. The resulting solid was stirred with hexane and filtered to afford the title product (58 g; 92%). C$_{15}$H$_{17}$N$_3$O$_2$, MW: 271.32.

EXAMPLE 30

[6-(4-methyl-1H-imidazol-1-yl)-2-(phenyl)]quinoline dihydrochloride

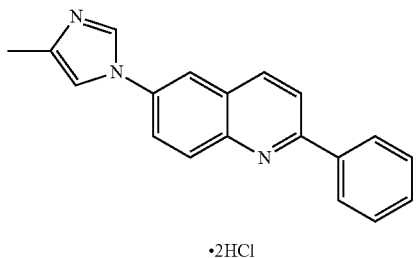 [SMILES: Cc1cn(-c2ccc3nc(-c4ccccc4)ccc3c2)cn1]

·2HCl 6-(4-methyl-1H-imidazol-1-yl)-2-(trifluoromethane sulfonoxy)quinoline (1.0 g; 2.9 mmol) was dissolved in toluene (60 mL), then K$_2$CO$_3$ (1.9 g, 9.35 mmol), palladium tetrakisthriphenylphosphine (0.40 g, 0.35 mmol), and phenylboronic acid (0.42, 3.9 mmol) were added under argon atmosphere. The resulting mixture was refluxed for 2 hours, then cooled at r.t. and quenched with water (100 mL). The organic phase was separated, the aqueous layer was extracted with toluene, and the combined organic phases were concentrated. The residue was taken up with dry toluene, concentrated again to small volume, then the hydrochloride was precipitated by bubbling gaseous HCl, to provide the title product as a light brown powder (380 mg, 36%) melting at: 285-289° C. C$_{19}$H$_{15}$N$_3$.2HCl, MW: 358.35. $^1$H-NMR (200 MHz, d$_6$-DMSO) ppm: 2.30 (s, 3H), 7.60 (m, 3H), 7.86 (d, 2H), 8.01 (d, 1H), 8.03 (s, 1H), 8.33-8.38 (m, 5H), 9.62 (s, 1H).

EXAMPLE 31

[6-(4-methyl-1H-imidazol-1-yl)-2-(4-methoxyphenyl)]quinoline dihydrochloride

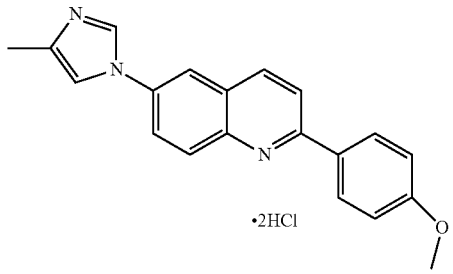 [SMILES: COc1ccc(-c2ccc3cc(-n4cnc(C)c4)ccc3n2)cc1]

·2HCl

Analogously prepared in 75% yield, using 4-methoxyphenylboronic acid in the Suzuky coupling. Crystallized from DCM/methanol, light yellow powder, m.p.: 276-278° C. dec. C$_{20}$H$_{17}$N$_3$O.2HCl, MW: 388.38. $^1$H-NMR (400 MHz, d$_6$-DMSO) ppm: 2.31 (s, 3H), 3.81 (s, 3H), 7.00 (d, 2H), 7.47 (s, 1H), 7.77 (d, 2H), 7.93 (t, 2H), 8.02 (s, 1H), 8.07 (d, 1H), 8.55 (d, 1H), 8.97 (s, 1H). FT-IR (ATR), cm$^{-1}$: 1640, 1596, 1511, 1368, 1298, 1261, 1184, 1015, 827.

EXAMPLE 32

[6-(4-methyl-1H-imidazol-1-yl)-2-(4-fluorophenyl)]quinoline dihydrochloride

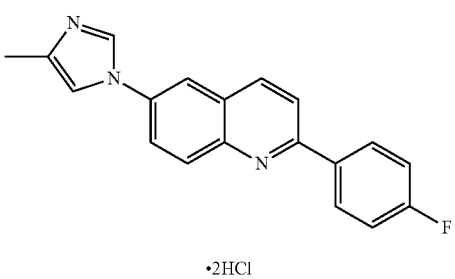 [SMILES: Cc1cn(-c2ccc3nc(-c4ccc(F)cc4)ccc3c2)cn1]

·2HCl

Analogously prepared in 83% yield, using 4-fluorophenylboronic acid in the Suzuky coupling. Crystallized from DCM/methanol, cream powder, m.p.: 264-268° C. C$_{19}$H$_{14}$FN$_3$.2HCl, MW: 376.34. MS (ESI) m/z: 304 (M+1). $^1$H-NMR (400 MHz, d$_6$-DMSO) ppm: 2.27 (s, 3H), 7.16 (t, 2H), 7.40 (s, 1H), 7.73-7.70 (m, 2H), 7.84 (t, 2H), 7.86 (s, 1H), 7.96 (d, 1H), 8.46 (d, 1H), 8.90 (s, 1H). FT-IR (ATR), cm$^{-1}$: 1615, 1597, 1537, 1510, 1458, 1369, 1329, 1249, 1170, 1079, 920, 840, 826.

EXAMPLE 33

[6-(4-methyl-1H-imidazol-1-yl)-2-(4-methylthiophenyl)]quinoline dihydrochloride

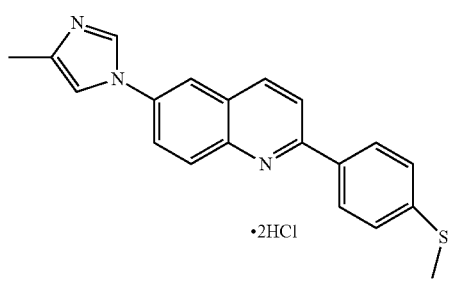 [SMILES: CSc1ccc(-c2ccc3cc(-n4cnc(C)c4)ccc3n2)cc1]

·2HCl

Analogously prepared in 71% yield, using 4-methylthiophenylboronic acid in the Suzuky coupling. Crystallized from DCM/methanol, light orange powder, m.p.: 294-296° C. C$_{20}$H$_{17}$N$_3$S.2HCl, MW: 404.34. MS (ESI) m/z: 332 (M+1). $^1$H-NMR (400 MHz, d$_6$-DMSO) ppm: 2.38 (s, 3H), 2.53 (s, 3H), 7.43 (d, 2H), 8.07-8.11 (m, 2H), 8.22-8.28 (m, 4H), 8.38

(s, 1H), 8.53 (d, 1H), 9.63 (s, 1H). FT-IR (ATR), cm⁻¹: 1588, 1545, 1418, 1361, 1192, 1095, 1063, 976, 938, 804, 797.

6-(4-methyl-1H-imidazol-1-yl)-2-(trifluoromethane sulfonoxy)quinoline

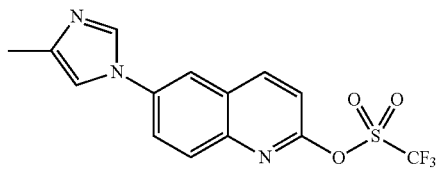 [SMILES: Cc1cn(-c2ccc3nc(OS(=O)(=O)C(F)(F)F)ccc3c2)cn1]

6-(4-methyl-1H-imidazol-1yl)-2-quinolinone (8.53 g; 28.7 mmol) was dissolved in DMF (80 mL), then NaH (3.4 g, 60% dispersion in mineral oil, 85.4 mmol) was added portion-wise, under argon, at −7° C. The resulting mixture was stirred at 0° C. for 15 min. then cooled at −15° C., and bis(trifluoromethylsulfonyl)phenylamine (13.3 g, 40.1 mmol), dissolved in dry DMF (35 mL) was added drop-wise. The resulting mixture was stirred at −5° C. for 20 min. then allowed to come to r.t. and stirred at that temperature for 1 hour. The reaction mixture is then poured in water (300 mL), the resulting precipitate is filtered and dried by co-evaporation with DCM. The product is then stirred with hexane few minutes, filtered and dried to provide the title product as brown crystals, (8.0 g; yield: 79%), m.p.: 150.4-152.1° C. $C_{14}H_{10}F_3N_3O_3S$, MW: 357.3; MS (ESI) m/z: 358 (M+1).

6-(2-methyl-1H-imidazol-1-yl)-2-hydroxy-quinoline hydrochloride

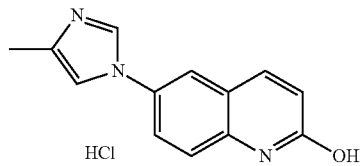 [SMILES: Cc1cn(-c2ccc3nc(O)ccc3c2)cn1 ; Cl]

3-ethoxy-N-[4-(4-methyl-1H-imidazol-1-yl)phenyl]acrylamide (18.0 g; 6.8 mmol) was added at −5/−10° C. to concentrated sulfuric acid (100 mL) and the resulting mixture was stirred at r.t. for 25 hrs. The reaction mixture was quenched in ice/water (400 g), and stirred for further 30 min., then the pH was adjusted to pH=8 by adding $K_2CO_3$. The precipitate was extracted using AcOEt/MeOH (9:1; 4×150 mL), the combined organic extracts were dried and concentrated. The residue was taken up with isopropanol (70 mL) and aqueous HCl (6 N, 15 mL) was added at +5° C. under stirring, the resulting precipitate was filtered, washed with isopropanol, then with isopropyl ether, and dried to afford 8.53 g (44%) of the title compounds as a brown solid, m.p.: 274-277° C.

3-ethoxy-N-[4-(4-methyl-1H-imidazol-1-yl)phenyl]acrylamide

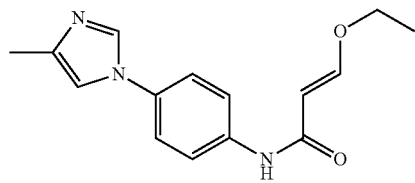 [SMILES: CCO/C=C/C(=O)Nc1ccc(-n2cnc(C)c2)cc1]

4-(4-methyl-1H-imidazol-1-yl)aniline (15 g, 138 mmol) was dissolved in dry pyridine (80 mL), freshly distilled 3-ethoxyacryloyl chloride (19 g, 140 mmol) was then added drop-wise at 5°/0° C. The resulting mixture was stirred at 0° C. for 1 hours and at r.t. overnight. The reaction mixture was quenched with water (500 mL), the pH was adjusted to pH=10, by adding $K_2CO_3$ and the resulting solid was filtered, washed with water and dried, to provide the title product as slight orange powder (18.6 g; 75%), m.p.: 214-216° C. $C_{15}H_{17}N_3O_2$, MW: 271.32.

4-(4-methyl-1H-imidazol-1-yl)aniline

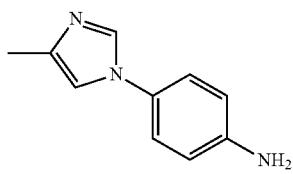

4-(4-methyl-1H-imidazol-1-yl)nitrobenzene (22.5 g; 0.87 mmol) is dissolved in abs. ethanol (250 mL), then $SnCl_2.2H_2O$ (125 g; 0.55 mol) is added portion-wise, on cooling at 0° C. The resulting mixture is stirred at r.t. for 2 hours and heated at reflux overnight. The reaction mixture is then cooled at r.t. and the pH is adjusted to 12, by adding 30% KOH (500 mL), then KOH pellets under stirring. The resulting suspension is filtered and the cake is washed with ethanol, the combined filtrate and washings are concentrated and the residue is extracted with DCM. Concentration of the combined organic extracts afforded the title product as a slight brown solid (15.3 g; 80%), m.p.: 122-125° C. $C_{10}H_{11}N_3$, MW 173.22.

4-(4-methyl-1H-imidazol-1-yl)nitrobenzene

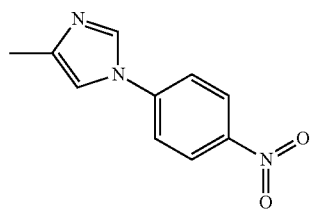

4-fluoronitrobenzene (32.3 g; 0.229 mol) and 4-methyl-1H-imidazole (25 g; 0.3 mol) are mixed at r.t., to this stirred mixture $K_2CO_3$ (44 g; 0.3 mol) is added. The reaction mixture is then heated at 120° C. overnight, then cooled at r.t. and poured in water (2 L), the resulting suspension is filtered and washed with water. The obtained solid is dried at 60° C. and recrystallized from ethyl acetate (600 mL), to provide the title compound as a yellow solid (22.5 g; 48.3%). The regioisomer, 4-(5-methyl-1H-imidazol-1yl)nitrobenzene remains in the crystallization mother liquor along with a certain amount of the titled product (TLC: hexane/AcOEt 3:2). $C_{10}H_9N_3O_2$, MW 203.2.

Pharmacological Evaluation of the Compounds of the Invention
Binding Study Towards $I_2$ Imidazoline Receptor Subtype in Rat Brain.

Experiments were performed according to the procedure of Lione L A et al., 1998 (Eur. J. Pharmacol., 353:123-135). Male Wistar rats (240-300 g, Harlan, Italy) were sacrificed by decapitation. Whole brains were immediately removed on ice and homogenised in 10 volumes of buffered sucrose (0.32M in 50 mM Tris-HCl, pH 7.4 at 4° C.) using a motor driven Teflon-glass homogeniser. The homogenate was centrifuged at 1000×g for 10 min at 4° C. The resultant supernatants were pooled and centrifuged at 32000×g for 20 min at 4° C. The supernatants were discarded and each pellet suspended in 10 volumes of assay buffer (50 mM Tris-HCl, 1 mM MgCl2, pH 7.4 at 4° C.) and spun at 32000×g for 20 min at 4° C. The pellets were washed twice by repeated centrifugation at 32000×g for 20 min at 4° C. The final pellets were stored at −80° C. until use. Prior to radioligand binding studies, membrane pellets were thawed and washed a further 4 times by re-suspension in 10 volumes of assay buffer (as above) and repeated centrifugation to remove any possible endogenous inhibitors of binding. The protein content of the membrane preparations was determined, using bovine serum albumin as the standard (Bradford M, 1976, Anal. Biochem., 72:248-254). For routine procedures (competition binding assays) 250 µl of membranes suspension (2 mg protein/ml) were incubated with [3H]-2BFI (2.5×10-9 M; GE Healthcare, 66 Ci/mmol), in the absence or presence of various concentration of test compounds. Non specific binding was determined in the presence of 10-5 M BU224 (Tocris Bioscience). The incubation, in a final volume of 1 ml, was performed in polystyrene multiwell 24, started adding membranes suspension and was carried out for 90 min at 25° C. With the exception of total binding and non specific binding, all concentration points were performed in duplicate. Compounds were tested in 3-5 different concentrations, ranging from 10-10 M to 10-5 M final concentration. The affinity expressed as $IC_{50}$ value (concentration which has a 50% displacing potency) was calculated by linear regression (log µM concentration of test compound vs. % specific residual binding B/Bo).

Monoaminooxidase (MAO) Activity Assay.

Inhibitory activity of compounds was evaluated by a homogeneous luminescent method, the MAO-Glo™ Assay (Promega), measuring the monoamine oxidase activity (MAOs) from recombinant source (microsomes from baculovirus infected insect cells, Sigma). Experiments were performed according to the Supplier's procedure, incubating human recombinant MAO-A or MAO-B with a luminogenic substrate, a derivative of beetle luciferin ((4S)-4,5-dihydro-2-(6-hydroxybenzothiazolyl)-4-thiazolecarboxylic acid). MAOs converts this luciferin derivative to methyl ester luciferin and only compounds that interfere with the ability of the enzyme to use the pro-luminescent substrate will cause changes in the resulting luminescent signal. The MAO-Glo™ Assay was performed in two steps:

Step 1. The MAO reaction: MAO substrate was incubated with MAO-A or MAO-B (1 µg/sample) in the absence (Total activity) or presence (modulated activity) of test compounds. Total activity was determined in the presence the appropriate solvent. The substrate concentrations for MAO-A and MAO-B correspond to their apparent Km (40 µM and 4 µM, respectively). Reaction started adding the enzyme solution and samples were incubated for 60 min at room temperature. For negative control reaction, samples of MAO reaction buffer (100 mM Hepes, 5% glycerol, pH 7.5) indeed the test compound were included. For MAO-B activity assay, MAO reaction buffer contain 10% DMSO, in order to increase enzymatic activity.

Step 2. Luciferin Detection: The methyl ester luciferin, produced in step 1 by the action of MAO on the MAO substrate, reacts with esterase and luciferase (detection reagent) to generate light. At the end of incubation 50 µl of Luciferin Detection reagent were added to each well, plate was incubated at room temperature for 20 min, then luminescent signal was detected by luminometer (integration time 0.25-1 sec per well). Values were displayed as relative light unit (RLU). Net MAO-dependent luminescence (net RLU) were calculated by subtracting the average luminescence of the negative control reaction without MAO enzyme. A reduction of net signal in the presence of test compound, with respect to total activity, reflect its effect on MAOs activity. All compounds were initially tested at 10-5 M final concentration, then inhibition curves for active compounds, spanning in at least two order of magnitude concentrations, were performed. A percentage of inhibition for each concentration tested were calculated and the $IC_{50}$ value was estimated by linear regression.

TABLE 2

$I_2$ Imidazoline Receptor Binding & Monoaminooxidase (MAO) activity assay.

| Compound | [³H]2-BFI binding $IC_{50}$ (µM) | MAO A activity $IC_{50}$ (µM) | MAO B activity $IC_{50}$ (µM) |
| --- | --- | --- | --- |
| Example 1 | 0.68 | 0.22 | >10 |
| Example 2 | 2.40 | >10 | >10 |
| Example 4 | 0.48 | 2.06 | >10 |
| Example 5 | 1.18 | >10 | >10 |
| Example 6 | 1.16 | >10 | >10 |
| Example 7 | 2.18 | >10 | >10 |
| Example 9 | 1.04 | >10 | >10 |
| Example 13 | 1.34 | 10 | >10 |
| Example 14 | 0.61 | 0.35 | >10 |
| Example 15 | 0.50 | >10 | >10 |
| Example 16 | 0.19 | >10 | >10 |
| Example 17 | 0.42 | 1.13 | 10 |
| Example 18 | 1.90 | 0.67 | >10 |
| Example 19 | 3.16 | >10 | >10 |
| Example 20 | 1.19 | 0.25 | >10 |
| Example 21 | 0.24 | >10 | >10 |
| Example 22 | 3.78 | 2.09 | 1.49 |
| Example 23 | 0.82 | 0.15 | >10 |
| Example 24 | 1.14 | 0.28 | >10 |
| Example 25 | 0.85 | 0.45 | >10 |
| Agmatine | >10 | >100 | >100 |
| 2-BFI | 0.007 | >1 | >1 |
| Idazoxan | 0.011 | >1 | >1 |
| Clorgyline | 1.53 | 0.027 | 14.30 |
| Deprenyl | 2.31 | 19.10 | 0.48 |

These in vitro data highlights how within the group of compounds of formula (I) it is possible by changing the substitution pattern to modulate $I_2$ Receptor, MAO-A and MAO-B enzymes activity. For instance, introduction of methyl onto imidazol ring allows to retain activity towards $I_2$ Receptor while losing MAO inhibitory activity (see for instance compounds at examples 2 and 5 vs. example 1), same effect is obtained with an appropriate substitution both at the imidazol and at the phenyl in position 2 (see for instance compounds at examples 6 and 9 vs. example 1). Appropriate substitution at the phenyl in position 2 can also modulate MAO-A vs. MAO-B activity (see for instance compound at examples 22 vs. example 17). Accordingly, compounds of the invention can be either selective $I_2$ Receptor agonists, endowed with striking in vitro potencies, or balanced $I_2$ Receptor agonists/MAO-A vs. MAO-B inhibitors.

Tail Suspension Test in Mice

To evaluate novel antidepressants compounds several animal models have been developed. Among them, the tail suspension test is a simple, fast and convenient model in which many antidepressants reduce the immobility time, indicating that this parameter can be used as an index of antidepressant activity. The antidepressant effect of representative examples of compounds of formula (I) has been evaluated according to the procedure below. The immobility was induced according to the procedure of Stem et al. (1985). CD1 Mice (Harlan, Italy) were individually suspended 75 cm above the top with an adhesive tape placed 1 cm from the tip of the tail. Immobility duration was recorded for 5 min. Mice were considered immobile only when they hung passively and completely motionless. Compounds were given orally, 30 min before the test at doses ranging between 0.3 and 30 mg/kg. Data collected were expressed as mean percent effect (MPE), which represents the % of inhibition in immobility time between the animals treated with representative compounds of formula (I) and the controls that received only the vehicle. From the MPE data, the dose yielding a reduction of 50% ($ED_{50}$) has been calculated.

TABLE 3

| Compound | Dose mg/Kg; OS | MPE | $ED_{50}$ mg/Kg; OS |
|---|---|---|---|
| Example 1 | 0.3 | 35 | 4.8 |
|  | 1 | 38 |  |
|  | 3 | 40 |  |
|  | 10 | 66 |  |
|  | 30 | 84 |  |
| Example 2 | 3 | 17 | 7.1 |
|  | 10 | 77 |  |
|  | 30 | 83 |  |
| Example 5 | 3 | 41 | 4.9 |
|  | 10 | 61 |  |
|  | 30 | 91 |  |
| Example 16 | 3 | 41 | 4.6 |
|  | 10 | 66 |  |
|  | 30 | 100 |  |
| Example 21 | 3 | 36 | 4.9 |
|  | 10 | 72 |  |
|  | 30 | 89 |  |
| Example 25 | 3 | 23 | 8.7 |
|  | 10 | 54 |  |
|  | 30 | 40 |  |

| Commercially available antidepressant drugs | Reference | $ED_{50}$ mg/Kg; SC |
|---|---|---|
| Reboxetine | Millan MJ et al., 2001 JPET, 298(2): 581-591 | 4.2 |
| Citalopram | Millan MJ et al., 2001 JPET, 298(2): 581-591 | 8.8 |
| Venlafaxine | Millan MJ et al., 2001 JPET, 298(2): 581-591 | 11.7 |

Mice treated with representative compounds of formula (I) exhibited dose-dependent antidepressant-like activities in the "Tail Suspension Test" as compared with standard reference drugs.

TABLE 4

| Compound | Dose mg/Kg; OS | MPE | $ED_{50}$ mg/Kg; OS |
|---|---|---|---|
| Example 1 | 3 | 43 | 5.1 |
|  | 10 | 54 |  |
|  | 30 | 97 |  |
| Example 1 + Idazoxan 0.3 mg/Kg; IP | 3 | 7 | NC |
|  | 10 | 39 |  |
|  | 30 | 43 |  |

NC: not computable

As showed in table 4, the antidepressant-like effect of—Example 1—was blocked (dose-response shifted to the right) by the presence of a commercially available antagonist of imidazoline (I2) receptors (0.3 mg/Kg Idazoxan). This effect was fully in agreement with "in vitro" data showed in table 2 where representative compounds object of the present invention were able to inhibit the binding of [$^3$H]2-BFI with $IC_{50}$ in the low micromolar range. This means that the behavioural antidepressant-like effect of representative compounds of formula (I) could be mediated, at least in part, by their interaction with imidazoline (I2) receptors.

CFA Model of Inflammatory Pain in Rats: Effect of a Representative Compound of Formula (I) in Potentiating the Effect of a Low Dose of Morphine The effects of compounds of formula (I) were evaluated in an animal model of chronic inflammatory pain. In particular, it has been investigated their potential ability to increase the absolute analgesic power of a low dose of morphine. Recently, it has been shown that the use of Complete Freund's Adjuvant (CFA; Mycobacterium tuberculosis) as a triggering agent for the inflammatory response, along with the use of an appropriate protocol, is a suitable model of chronic pain. CFA-induced prolonged inflammation has been used extensively in studies of behavioural pain response (K. Walker, Mol Med Today, 1999, 5, 319-321), since it has been considered also suitable for studying involvement of neuronal plasticity in chronic pain (R. Sharif Naeini, Eur. J. Neuroscience, 2005, 22, 8, 2005-2015). Experiments are performed as described in the literature (C. J. Woolf, Br. J. of Pharmacology, 1997, 121, 417-424); 6 rats were used for each group, each product was tested with a single oral dose of 1.5 mg/Kg in the presence or absence of a fixed low dose of morphine (0.5 mg/Kg; subcutaneously). Compounds of formula (I) were administered 24 hours after the interplantar challenge, and the analgesic activity was measured starting from the 24 hours following the challenge. In Table 5, results obtained in the CFA model, for a representative compound of formula (I), co-administered with a low dose of morphine, are listed in comparison to the same dose of morphine administered alone. Analgesic effect was assessed using the Randall-Selitto model. Results are reported as mean percent effect (MPE) which represents the difference (%) in pain threshold between the animals treated with the drugs and the controls that received only the vehicle (reduction of the nociceptive effect, due to paw loading with increasing weight, in comparison to controls which received CFA treatment). 100% protection means that the animals treated with the compounds and CFA can tolerate the same stimulus (weight) as the control animal which has not received CFA treatment.

TABLE 5

| Compound | Dose mg/Kg; OS | MPE 2 h | % effect | MPE 3 h | % effect | MPE 4 h | % effect |
|---|---|---|---|---|---|---|---|
| Example 1 | 1.5 | 17.19 | | 6.61 | | 2.46 | |
| Morphine 0.5 mg/Kg; SC | — | 42.88 | — | 30.49 | — | 15.04 | — |
| Example 1 + Morphine 0.5 mg/Kg; SC | 1.5 | 98.30 | +129 | 90.73 | +198 | 82.46 | +448 |

The representative compound of formula (I)—Example 1—administered orally at a dose not able to induce analgesic-like effects by its own, demonstrated a pronounced sparing effect when administered as add-on with a low dose of morphine. Moreover, the increase in potency due to the treatment was linked to an outstanding and surprising increase in the duration of the analgesic effect. The absolute analgesic effect of the add-on treatment was 2.29, 2.98 and 5.48 times more efficacious than morphine alone 2, 3 and 4 hours after drug administration, respectively. The effect at 4 hours is particularly relevant, since at this time the animals treated with morphine alone showed a very minor reduction of hyperalgesia, while the animal co-administered with morphine and the compound at Example 1, were still almost completely protected from hyperalgesia.

Pharmaceutical Compositions

Compounds of formula I, their salts and solvates thereof, can be used in the manufacture of a suitable medication for the therapeutic treatment of Depression and Anxiety as above specified, for the pharmacological treatment of Parkinson's disease, for the pharmacological treatment of the withdrawal symptoms for alcohol, tobacco and narcotics abuse, including Cocaine abuse, and to avoid remission episodes. In addition, compounds of formula (I), their salts and solvates thereof, can be used alone or in combination with morphine or other opioid drugs in the manufacture of a suitable medication for potentiation of the opioid pharmacological action and/or for the dosage reduction of the opioid drug. Finally, compounds of formula (I), their salts and solvates thereof, can be used in the manufacture of a suitable medication for the treatment of tolerance and dependence due to opioid drugs use. The compounds of the present invention may be administered orally or parenterally. The term parenteral used herein includes intravenous, intramuscular, subcutaneous. For all methods of treatment herein discussed for compounds of formula (I), its salt or solvate, the daily oral dosage regimen will preferably be from about 0.1 to about 20 mg/Kg of total body weight. It will also be recognised by one of skill in the art that the optimal quantity and spacing of individual dosages of a compound of formula (I) will be determined by the nature and extent of the condition being treated. This invention also relates to a composition suitable for the treatment of the above diseases, containing a pharmaceutically effective amount of a compound of formula (I), its salts or solvates, and a pharmaceutically acceptable carrier or diluent. In order to use a compound of formula (I) in therapy, it will normally be formulated into a dosage form in accordance with conventional methods of pharmacy and current guidelines and relevant good laboratory and manufacturing practices. The preferred route of administration for the compounds of the invention is oral. The compounds of the invention can be formulated in a wide variety of oral dosage forms, such as capsules, tablets, pills, powders and dispersible granules. Suitable carriers can be one or more substances which may also act as diluents, flavouring agents, solubilizer, lubricants, suspending agents, binders. Suitable carriers include but are not limited to magnesium carbonate, magnesium stearate, talc, lactose, pectin, dextrin, starch, methylcellulose, sodium carboxymethyl cellulose, cocoa butter and the like. Techniques used to prepare oral formulations are the conventional mixing, granulation and compression or capsules filling. Other forms suitable for oral administration include emulsions, syrups and aqueous solutions. Emulsions can be prepared using emulsifying agents for example lecithin, propylene glycol or sorbitan monooleate. Aqueous solutions can be prepared by dissolving the active component in water and adding suitable colorants, flavours, stabilising agents.

The compounds of the present invention may be formulated for parenteral administration (e.g., by injection or by continuous infusion) as a composition with suitable carriers including aqueous vehicles solutions (i.e.: saline, dextrose) or and/or oily emulsions. The drug product may be presented in unit dose forms, for example in ampoules or pre-filled syringes.

The invention claimed is:

1. A method for the treatment of depression, comprising administering a compound of formula (I), a pharmaceutically acceptable salt or solvate thereof, as the sole active agent to treat depression to a subject in need of treatment:

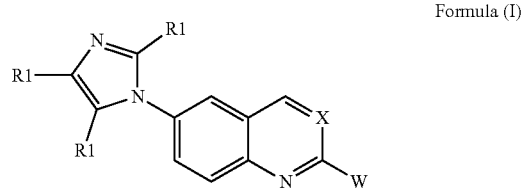

Formula (I)

wherein:
X is independently selected from —CH group or a nitrogen atom (—N);
W is independently selected from an aryl group, an heteroaryl or an heteroaryl group of

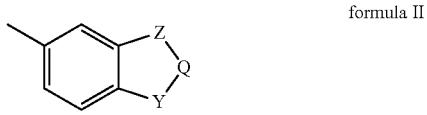

formula II

Heteroaryl group of Formula II:
wherein said aryl group is an unsubstituted or substituted phenyl, with one or more substituents independently selected from a halogen selected from the group consisting of fluorine (—F), chlorine (—Cl) and bromine (—Br), trifluoromethyl (—$CF_3$), alkyl, hydroxyl (—OH), alkoxy, trifluoromethoxy (—$OCF_3$), cyano (—CN), carboxamido selected from the group consisting of —$CONHR_3$, —$NHCOR_3$, —$CONR_2R_3$ and —$NR_2COR_3$, carbonyl, alkylthio, thiol, sulfinyl and sulfonyl wherein $R_2$ and $R_3$ are as defined below;
when W is an heteroaryl group it is independently selected from the following penta- or hexa-atomic heterocycles: 2-furyl, 3-furyl, 2-thienyl, 3-thienyl, pyrrole-2-yl, pyrrole-3-yl, pyridine-4-yl, pyridine-3-yl, pyrimidin-4-yl, wherein the heterocyclic ring may be substituted with one or two substituents independently selected from: $R_1$, alkoxy or hydroxy (—OH), wherein $R_1$ and $R_2$ are as defined below;

when W is an heteroaryl group of formula II, it is a benzo-condensed-5 or -6 membered heterocycle, wherein:

Z and Y are independently selected from: an oxygen atom (—O—), a sulphur atom (—S—), or the groups: —CHR$_3$—, —CR$_3$=, —NH—, —N=;

Q is independently selected from the groups: —CHR$_3$—, —CH=, —CR$_3$=, —CHR$_3$—CH$_2$—; provided that the combination of Y, Z, Q groups give rise to: 1,3-benzodioxole, benzofuran, 2,3-dihydrobenzofuran, benzothiophene, 2,3-dihydrobenzothiophene, indole, 2,3-dihydroindole, benzimidazole, benzoxazole, benzothiazole, 2H-3,4-dihydrobenzopyran, [1,4]-benzodioxine, 2,3-dihydro-[1,4]-benzodioxine (1,4-benzodioxan);

R$_1$ is independently selected from hydrogen (—H) or C$_1$-C$_4$ alkyl or hydroxymethyl (—CH$_2$OH), aminomethyl (—CH$_2$NH$_2$), alkylaminomethyl, di-alkylaminomethyl, trifluoromethyl (—CF$_3$); the C$_1$-C$_4$ alkyl group is a linear or branched saturated or unsaturated C$_1$-C$_4$ hydrocarbon chain; provided that in compounds of formula (I) not more than two R$_1$ groups substituting the imidazole ring, are simultaneously C$_1$-C$_4$ alkyl or trifluoromethyl (—CF$_3$) and only one R$_1$ group is hydroxymethyl (—CH$_2$OH), aminomethyl (—CH$_2$NH$_2$) alkylaminomethyl, di-alkylaminomethyl;

R$_2$ is a C$_1$-C$_6$ alkyl chain; herein the C$_1$-C$_6$ alkyl chain is intended as above defined for C$_1$-C$_4$ but optionally substituted with an aryl, aryl being herein as defined above;

R$_3$ is independently selected from hydrogen, C$_1$-C$_4$ alkyl as defined above for R$_1$; including all the possible tautomers of compounds of formula (I).

2. The method according to claim 1, wherein in formula (I), W is an heteroaryl group independently selected from the following penta- or hexa-atomic heterocycles: 2-furyl, 3-furyl, 2-thienyl, 3-thienyl, pyrrole-2-yl, pyrrole-3-yl, pyridine-4-yl, pyridine-3-yl, pyrimidin-4-yl; the heterocyclic ring being optionally substituted with one or two substituents independently selected from: R$_1$, alkoxy or hydroxy (—OH), wherein R$_1$ and R$_2$ are as defined in claim 1.

3. The method according to claim 1, wherein in formula (I), the substituent R$_1$ at the imidazole ring is methyl, said compound being selected from the group consisting of: [6-(2-methyl-1H-imidazol-1-yl)-2-phenyl]quinazoline; [6-(2-methyl-1H-imidazol-1-yl)-2-(4-methoxyphenyl)]quinazoline; [6-(4-methyl-1H-imidazol-1-yl)-2-phenyl]quinazoline; [6-(5-methyl-1H-imidazol-1-yl)-2-phenyl]quinazoline; [6-(4-methyl-1H-imidazol-1-yl)-2-(4-methoxyphenyl)]quinazoline; [6-(4-methyl-1H-imidazol-1-yl)-2-(2-methoxyphenyl)]quinazoline; [6-(4-methyl-1H-imidazol-1-yl)-2-(3-methoxyphenyl)]quinazoline; [6-(4-1H-imidazol-1-yl)-2-(1,3-benzodioxol-5-yl)]quinazoline; [6-(4-methyl-1H-imidazol-1-yl)-2-(4-fluorophenyl)]quinazoline; [6-(4-methyl-1H-imidazol-1-yl)-2-(4-metanesulfonylphenyl)]quinazoline; [6-(1H-imidazol-1-yl)-2-(4-methoxyphenyl)]quinoline; [6-(1H-imidazol-1-yl)-2-(2-methoxyphenyl)]quinoline; [6-(1H-imidazol-1-yl)-2-(1,3-benzodioxol-5-yl)]quinoline; [6-(1H-imidazol-1-yl)-2-(4-fluorophenyl)]quinoline; [6-(1H-imidazol-1-yl)-2-(4-dimethylaminophenyl)]quinoline; [6-(1H-imidazol-1-yl)-2-(4-trifluoromethoxyphenyl)]quinoline; [6-(1H-imidazol-1-yl)-2-(2-methyl-4-trifluoromethoxyphenyl)]quinoline; [6-(1H-imidazol-1-yl)-2-(4-dimethylaminophenyl)]quinoline; [6-(1H-imidazol-1-yl)-2-(4-methansulfonylphenyl)]quinoline; [6-(2-methyl-1H-imidazol-1-yl)-2-(4-methoxyphenyl)]quinoline; [6-(2-methyl-1H-imidazol-1-yl)-2-(2-methoxyphenyl)]quinoline; [6-(4-methyl-1H-imidazol-1-yl)-2-phenyl)]quinoline; [6-(4-methyl-1H-imidazol-1-yl)-2-(4-methoxyphenyl)]quinoline; [6-(4-methyl-1H-imidazol-1-yl)-2-(4-fluorophenyl)]quinoline; and [6-(4-methyl-1H-imidazol-1-yl)-2-(4-methylthiophenyl)]quinoline.

* * * * *